United States Patent
Lo et al.

(10) Patent No.: US 9,480,712 B2
(45) Date of Patent: Nov. 1, 2016

(54) BIOMEDICAL COMPOSITION

(71) Applicant: INDUSTRIAL TECHNOLOGY RESEARCH INSTITUTE, Hsinchu (TW)

(72) Inventors: Ya-Chin Lo, Taichung (TW); Hsiang-Fa Liang, New Taipei (TW); Ming-Cheng Wei, Yangmei (TW); Maggie J. M. Lu, Zhudong Township (TW); Min-Ying Lin, Hsinchu (TW); Chih-Peng Liu, Hsinchu (TW); Chun-Min Liu, Hsinchu (TW); Hsiang-Wen Tseng, New Taipei (TW); Tse-Min Teng, Ji'an Township (TW); Jui-Hsiang Chen, Hsinchu (TW); Yi-Man Chou, Taichung (TW); Yi-Ting Hsieh, Yangmei (TW); Chia-Mu Tu, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/514,137

(22) Filed: Oct. 14, 2014

(65) Prior Publication Data
US 2015/0118322 A1  Apr. 30, 2015

(30) Foreign Application Priority Data
Oct. 24, 2013  (TW) .............................. 102138398 A

(51) Int. Cl.
| | | |
|---|---|---|
| *C08B 37/08* | (2006.01) | |
| *A61K 47/48* | (2006.01) | |
| *A61K 31/704* | (2006.01) | |
| *A61K 31/4745* | (2006.01) | |
| *A61K 31/7036* | (2006.01) | |
| *A61K 33/24* | (2006.01) | |
| *A61K 45/06* | (2006.01) | |
| *A61K 31/4172* | (2006.01) | |
| *A61K 31/555* | (2006.01) | |
| *A61K 31/728* | (2006.01) | |

(52) U.S. Cl.
CPC ........... *A61K 33/24* (2013.01); *A61K 31/4172* (2013.01); *A61K 31/4745* (2013.01); *A61K 31/555* (2013.01); *A61K 31/704* (2013.01); *A61K 31/7036* (2013.01); *A61K 31/728* (2013.01); *A61K 45/06* (2013.01); *A61K 47/4823* (2013.01); *A61K 47/48038* (2013.01); *A61K 47/48853* (2013.01)

(58) Field of Classification Search
None
See application file for complete search history.

(56) References Cited

U.S. PATENT DOCUMENTS

| 4,582,865 A | 4/1986 | Balazs et al. |
|---|---|---|
| 6,117,455 A | 9/2000 | Takada et al. |
| 2007/0104654 A1 | 5/2007 | Hsieh et al. |
| 2008/0102114 A1 | 5/2008 | Koritala et al. |

FOREIGN PATENT DOCUMENTS

| JP | 61-187866 A | 8/1986 |
|---|---|---|
| TW | I250877 B | 3/2006 |
| TW | I310317 B | 6/2009 |
| TW | I314461 B | 9/2009 |

OTHER PUBLICATIONS

Wu et al. in J mater Sci: Mater Med (2012) 23:1921-1929.*
Choi et al. in Biomaterials 32 (2011) 1880-1889.*
Wu et al. in J. Mater Sci: Mater Med (2012) 23:1921-1929.*
Chang et al., "N-Boc-Histidine-Capped PLGA-PEG-PLGA as a Smart Polymer for Drug Delivery Sensitive to Tumor Extracellular pH", Macromolecular Bioscience, 2010, pp. 1248-1256, vol. 10.
Choi et al., "Hyaluronic acid-based nanocarriers for intracellular targeting: Interfacial interactions with proteins in cancer", Colloids and Surfaces B: Biointerfaces, 2012, pp. 82-94, vol. 99.
Choi et al., "Self-assembled hyaluronic acid nanoparticles for active tumor targeting", Biomaterials, 2010, pp. 106-114, vol. 31.
Choi et al., "Smart Nanocarrier Based on PEGylated Hyaluronic Acid for Cancer Therapy", ACS Nano, 2011, pp. 8591-8599, vol. 5, No. 11.
Luo et al., "Resonance Rayleigh scattering study of interaction of hyaluronic acid with ethyl violet dye and its analytical application", Biosensors and Bioelectronics, 2006, pp. 1186-1194, vol. 21.
Na et al.,"Self-Organized Nanogels Responding to Tumor Extracellular pH: pH-Dependent Drug Release and in Vitro Cytotoxicity against MCF-7 Cells", Bioconjugate Chemistry, 2007, pp. 1568-1574, vol. 18.
Nakaji-Hirabayashi et al., "Hyaluronic acid hydrogel loaded with genetically-engineered brain-derived neurotrophic factor as a neural cell carrier", Biomaterials, 2009, pp. 4581-4589, vol. 30.
Peer et al., "Physicochemical Evaluation of a Stability-Driven Approach to Drug Entrapment in Regular and in Surface-Modified Liposomes", Archives of Biochemistry and Biophysics, Nov. 15, 2000, pp. 185-190, vol. 383, No. 2.

(Continued)

*Primary Examiner* — Dennis Heyer
(74) *Attorney, Agent, or Firm* — Birch, Stewart, Kolasch & Birch, LLP

(57) ABSTRACT

The disclosure provides a biomedical composition, including: a hyaluronic acid; a modified histidine; and a polymer or $C_4$-$C_{20}$ alkane, wherein the modified histidine and the polymer or $C_4$-$C_{20}$ alkane are grafted to at least one primary hydroxyl group of the hyaluronic acid to allow the hyaluronic acid to form a hyaluronic acid derivative, wherein a graft ratio of the modified histidine is about 1-100%, and a graft ratio of the polymer or $C_4$-$C_{20}$ alkane is about 0-40%.

20 Claims, 15 Drawing Sheets

(56) References Cited

OTHER PUBLICATIONS

Sengupta et al., "Mimicking Tissue Surfaces by Supported Membrane Coupled Ultrathin Layer of Hyaluronic Acid", Langmuir, 2003, pp. 1775-1781, vol. 19.
Taiwan Office Action dated Jul. 22, 2014.
Tsai et al., "Hyaluronan-cisplatin conjugate nanoparticles embedded in Eudragit S100-coated pectin/alginate microbeads for colon drug delivery", International Journal of Nanomedicine, Jul. 2, 2013, pp. 2399-2407, vol. 8.
Wu et al., "Preparation and characterization of nanoparticles based on histidine-hyaluronic acid conjugates as doxorubicin carriers", Journal of Materials Science: Materials in Medicine, 2012, pp. 1921-1929, vol. 23.

* cited by examiner

BIOMEDICAL COMPOSITION

CROSS REFERENCE TO RELATED APPLICATION

The present application is based on, and claims priority from, Taiwan Application Serial Number 102138398, filed on Oct. 24, 2013, the disclosure of which is hereby incorporated by reference herein in its entirety.

TECHNICAL FIELD

The technical field relates to a biomedical composition.

BACKGROUND

Anti-cancer drugs in a form presently available on the market all have a problem of relating to a low drug-release rate. Although a low drug-release rate can decrease the side effects of anti-cancer drugs, the therapeutic effect of the drug cannot be increased.

Neovascularization of tumor tissue and inflammatory tissue is incomplete, and thus cell metabolic products cannot be easily excreted to a patient's circulatory system. Therefore, pH values of such tissues are lower than those of normal tissues, and are about 6.8-7.2. In addition, pH values of environments of endosomes and lysosomes in a cell are about 4.0-6.5, and if nano-carriers can be rapidly controlled to release a drug, the problem of low drug release rates among nano-carrier drugs can be solved. Furthermore, for some biotechnological drugs, such as peptides, proteins, and gene fragments, if this kind of drug is released from endosomes to cytoplasma, and is not transported to lysosomes, the activities of such drugs can be increased.

Hyaluronic acid is a polymer of disaccharides, themselves composed of D-glucuronic acid and D-N-acetylglucosamine. In the hyaluronic acid, D-glucuronic acid and D-N-acetylglucosamine are linked via β-1,3 glycosidic bonds, while disaccharides are linked via β-1,4 glycosidic bonds. Generally, molecular weights of hyaluronic acid range from 5,000 to 20,000,000 Da. Commercialized hyaluronic acid is usually in the form of sodium salt thereof, i.e. sodium hyaluronate.

Natural hyaluronic acid is a water-soluble polymer, has excellent variable properties for being a drug carrier, such as bio-compatibility, non-immunogenicity, natural degradation by an enzyme in the body, having a lot of functional groups of —OH, —COOH and —CH, OH, etc., and capable of performing covalent modification. Therefore, according to the afore mentioned information, it is known that hyaluronic acid is able to be an excellent drug carrier.

At present, a novel drug delivery system that has high bio-compatibility, and that can be designed to release a drug only in an appropriate environment, is needed.

SUMMARY

The disclosure provides a biomedical composition, comprising: a hyaluronic acid; a modified histidine; and a polymer or $C_4$-$C_{20}$ alkane, wherein the modified histidine and the polymer or $C_4$-$C_{20}$ alkane are grafted to at least one primary hydroxyl group of the hyaluronic acid to allow the hyaluronic acid to form a hyaluronic acid derivative, wherein a graft ratio of the modified histidine is about 1-100%, and a graft ratio of the polymer or $C_4$-$C_{20}$ alkane is about 0-40%.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION

Figure 1A:
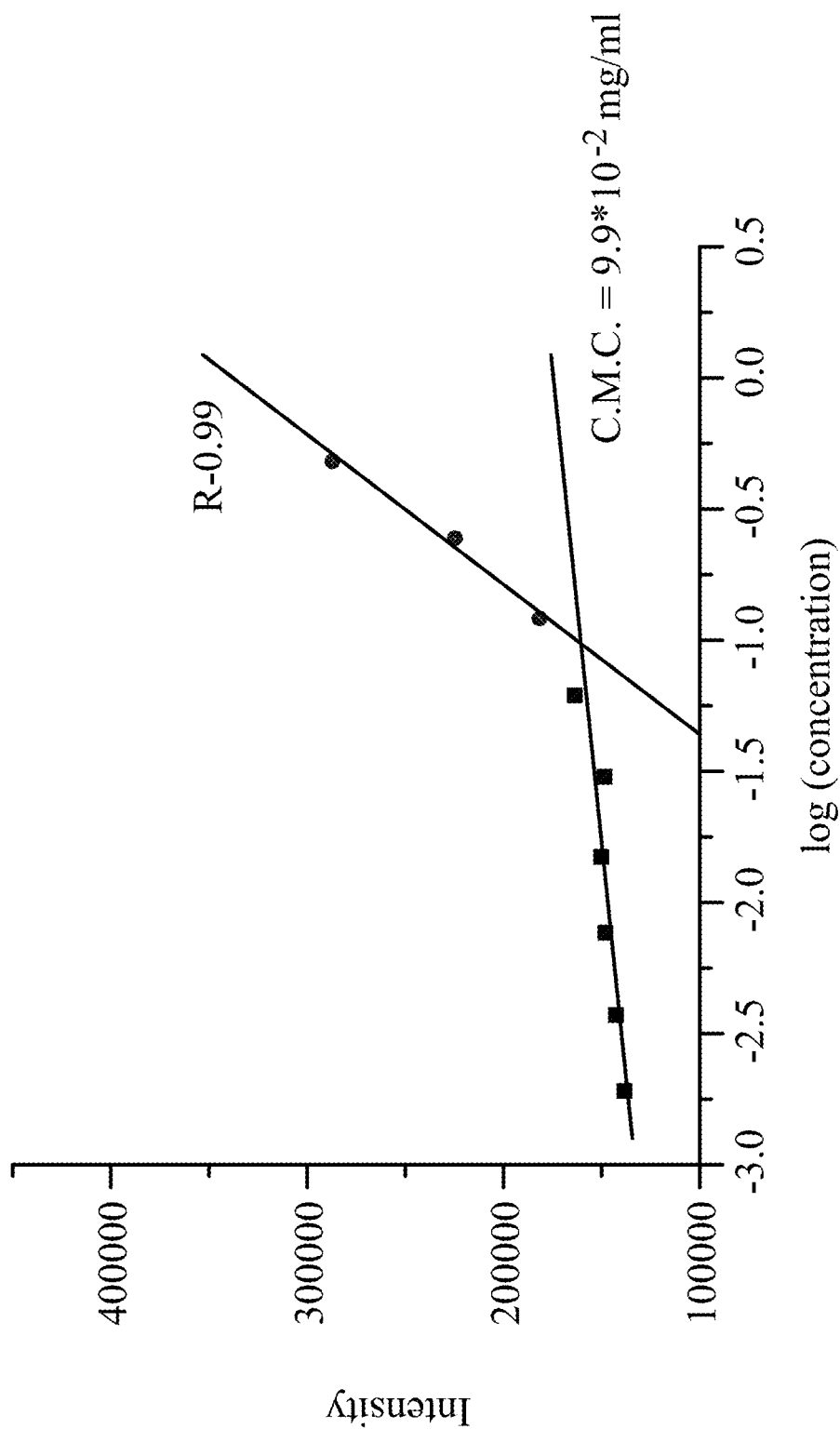
FIG. 1A shows the result of determining the critical micelle concentrations of the $HA_{16k}$-g-40% BocHis material at pH 7.4 according to an exemplary embodiment.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment of the present disclosure, the present disclosure provides a biomedical composition containing a hyaluronic acid derivative.

The biomedical composition of the present disclosure may comprise, but is not limited to, a hyaluronic acid, a modified histidine, and a polymer or $C_4$-$C_{20}$ alkane, wherein the modified histidine and the polymer or $C_4$-$C_{20}$ alkane are grafted to at least one primary hydroxyl group of the hyaluronic acid, and wherein the modified histidine, the polymer or $C_4$-$C_{20}$ alkane and the hyaluronic acid form a hyaluronic acid derivative.

A graft ratio of the modified histidine to the hyaluronic acid may be about 1-100%, however, it is noted that a graft ratio of the polymer or $C_4$-$C_{20}$ alkane to the hyaluronic acid is about 0-40%. Therefore, it is understood that the hyaluronic acid derivative may have or may not have the polymer or $C_4$-$C_{20}$ alkane grafted thereto. In other words, the biomedical composition of the present disclosure optionally comprises the polymer or $C_4$-$C_{20}$ alkane.

In one embodiment, a graft ratio of the modified histidine may be about 1-100% while a graft ratio of the polymer or $C_4$-$C_{20}$ alkane is 0, that is, the hyaluronic acid derivative mentioned above does not have the polymer or $C_4$-$C_{20}$ alkane grafted thereto. In this embodiment, an exemplificative formula for the hyaluronic acid derivative mentioned above may be shown as the following Formula (I), but it is not limited thereto:

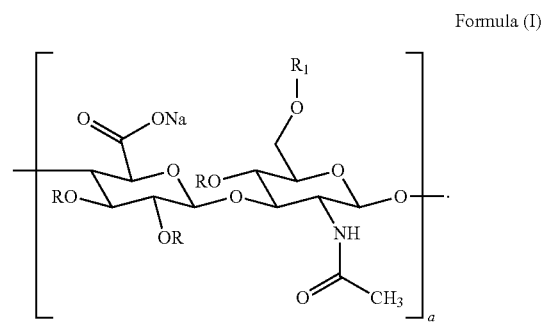

Formula (I)

In Formula (I), $R_1$ may be the modified histidine, and a may be a positive integer of 5-2000, but it is not limited thereto.

In other embodiments, the hyaluronic acid derivative mentioned above has the polymer or $C_4$-$C_{20}$ alkane grafted thereto, and in this embodiment, a graft ratio of the modified histidine may be about 1-100% while a graft ratio of the polymer or $C_4$-$C_{20}$ alkane is 1-40%. In this embodiment, an exemplificative formula for the hyaluronic acid derivative mentioned above may be shown as the following Formula (II), but is not limited thereto:

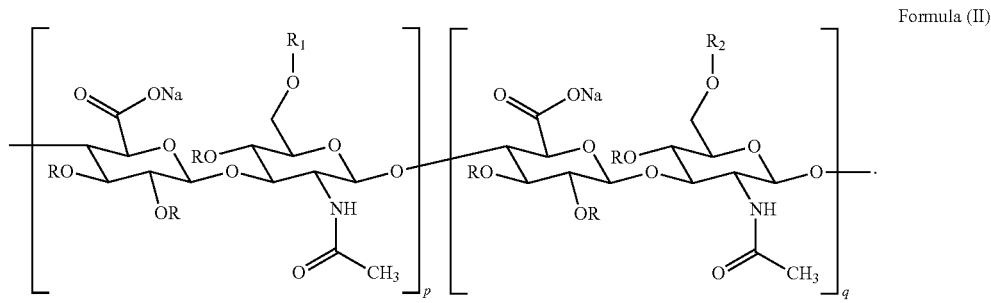

Formula (II)

In the Formula (II), $R_1$ may be the modified histidine, and $R_2$ may be the polymer or $C_4$-$C_{20}$ alkane. In addition, p and q are positive integers, and a ratio of p to q may be between 0.1-100, but is not limited thereto. In one embodiment, a ratio of p to q may be between 0.1-20.

In one embodiment, the at least one primary hydroxyl group of the hyaluronic acid mentioned above may comprise a hydroxyl group located on the fifth carbon atom of a N-acetyl-D-glucosamine of at least one disaccharide unit of the hyaluronic acid, but is not limited thereto.

In one embodiment, in the biomedical composition of the present disclosure, a molecular weight of the hyaluronic acid mentioned above is about 7,000-1,500,000. In another embodiment, in the biomedical composition of the present disclosure, a molecular weight of the hyaluronic acid mentioned above is about 7,000-350,000.

In the biomedical composition of the present disclosure, examples for suitable modified histidines may comprise, for example, Boc-histidine, Cbz-histidine, Fmoc-histidine and Ac-histidine, etc., but is not limited thereto.

Furthermore, in the biomedical composition of the present disclosure, the polymer comprises polyethylene glycol (PEG), polycaprolactone (PCL), poly lactic acid (PLA), polyglycolic acid (PGA), poly(lactic-co-glycolic acid) (PLGA) or polyvinylpyrrolidone (PVP), etc., but is not limited thereto.

Moreover, in the biomedical composition of the present disclosure, examples for the $C_4$-$C_{20}$ alkane may comprise, but is not limited to, $C_5H_{11}$, $C_7H_{15}$, $C_9H_{19}$, $C_{11}H_{23}$, etc.

In one embodiment, in the biomedical composition of the present disclosure, the modified histidine is Boc-histidine. Furthermore, in a specific embodiment, a graft ratio of the Boc-histidine is about 1-100%, and a graft ratio of the polymer or $C_4$-$C_{20}$ alkane is about 0.

In addition, in one embodiment, in the biomedical composition of the present disclosure, the preceding polymer may be polyethylene glycol (PEG), wherein a molecular weight may be about 300-10,000. Furthermore, in this embodiment, in the biomedical composition of the present disclosure, a graft ratio of the polymer may be about 1-40%. In a specific embodiment, the modified histidine is Boc-histidine and the preceding polymer may be polyethylene glycol (PEG), wherein a graft ratio of the Boc-histidine is about 1-80%, and a graft ratio of the polyethylene glycol (PEG) is about 1-30%.

In one embodiment, in the biomedical composition of the present disclosure, the $C_4$-$C_{20}$ alkane may be $C_{11}H_{23}$, and in this embodiment, a graft ratio of the $C_{11}H_{23}$ may be about 1-40%. In a specific embodiment, in the biomedical composition of the present disclosure, the modified histidine is the Boc-histidine, and the $C_4$-$C_{20}$ alkane may be $C_{11}H_{23}$, wherein a graft ratio of the Boc-histidine is about 1-80%, and a graft ratio of the $C_{11}H_{23}$ is about 1-30%.

In addition, in the biomedical composition of the present disclosure, a molecular weight of the preceding hyaluronic acid derivative formed by the modified histidine and the hyaluronic acid, or formed by the modified histidine, the polymer or $C_4$-$C_{20}$ alkane and the hyaluronic acid may be about 7,000-1,500,000. In one embodiment, a molecular weight of the preceding hyaluronic acid derivative may be about 7,000-1,200,000. In another embodiment, a molecular weight of the preceding hyaluronic acid derivative may be about 7,000-600,000.

In another embodiment of the present disclosure, the biomedical composition of the present disclosure may further comprise an active ingredient with a positive charge in water. In this embodiment, the active ingredient with a positive charge in water and a carboxyl group of the hyaluronic acid derivative attract each other due to different charge, and furthermore, by a hydrophobic effect produced from the modified histidine grafted on the hyaluronic acid and used to modify the hyaluronic acid, the active ingredient can be agglomerated, and make the active ingredient with a positive charge in water mentioned above be packaged in the preceding hyaluronic acid derivative.

In one embodiment, in the biomedical composition of the present disclosure, a weight ratio of the hyaluronic acid derivative mentioned above to the active ingredient with a positive charge in water mentioned above is about 1.25:1-50:1. In one embodiment, a weight ratio of the hyaluronic acid derivative mentioned above to the active ingredient with a positive charge in water mentioned above is about 1.25:1-25:1. In another embodiment, a weight ratio of the hyaluronic acid derivative mentioned above to the active ingredient with a positive charge in water mentioned above is about 2:1-25:1. In another embodiment, a weight ratio of the hyaluronic acid derivative mentioned above to the active ingredient with a positive charge in water mentioned above is about 2:1-10:1.

The above-mentioned active ingredient with a positive charge in water may comprise a drug (such as antibiotics, platinum-based antineoplastic drugs), nucleotide matter, peptides, or proteins, etc., but is not limited thereto.

In one embodiment, examples for the active ingredient with a positive charge in water may comprise, but is not limited to, doxorubicin, irinotecan, gentamicin, a platinum compound, etc.

Examples for the platinum compound may comprise, but is not limited to dichloro(1,2-diaminocyclohexane)platinum (DACHPt), cisplatin, oxaliplatin etc.

In one embodiment, in the biomedical composition of the present disclosure, the modified histidine mentioned above may be Boc-histidine and a graft ratio of the polymer or $C_4$-$C_{20}$ alkane mentioned above is 0 (that is, the hyaluronic acid derivative only has Boc-histidine grafted thereto), and the active ingredient with a positive charge in water may be doxorubicin, irinotecan, gentamicin or a platinum compound (such as, dichloro(1,2-diaminocyclohexane)platinum (DACHPt)). In this embodiment, the at least one primary hydroxyl group of the hyaluronic acid which has the modified histidine grafted thereto may comprise a hydroxyl group located on the fifth carbon atom of a N-acetyl-D-glucosamine of at least one disaccharide unit of the hyaluronic acid, but is not limited thereto. Furthermore, in this embodiment, a graft ratio of the Boc-histidine may be about 1-80%, and a weight ratio of the hyaluronic acid derivative to the active ingredient with a positive charge in water is about 1.25:1-25:1.

In another embodiment, in the biomedical composition of the present disclosure, the modified histidine mentioned above may be Boc-histidine, and the polymer mentioned above may be polyethylene glycol (PEG), and the active ingredient with a positive charge in water may be doxorubicin, irinotecan, gentamicin or a platinum compound (such as dichloro(1,2-diaminocyclohexane)platinum (DACHPt)). In this embodiment, the at least one primary hydroxyl group of the hyaluronic acid which has the modified histidine grafted thereto may comprise a hydroxyl group located on the fifth carbon atom of a N-acetyl-D-glucosamine of at least one disaccharide unit of the hyaluronic acid, but is not limited thereto. Furthermore, in this embodiment, a graft ratio of the Boc-histidine may be about 1-80%, a graft ratio of the polyethylene glycol (PEG) may be about 1-30%, and a weight ratio of the hyaluronic acid derivative to the active ingredient with a positive charge in water is about 3:1:1-50:1.

In another embodiment, in the biomedical composition of the present disclosure, the modified histidine mentioned above may be Boc-histidine, and the $C_4$-$C_{20}$ alkane mentioned above may be $C_{11}H_{23}$, and the active ingredient with a positive charge in water may be doxorubicin, irinotecan, gentamicin or a platinum compound (such as dichloro(1,2-diaminocyclohexane)platinum (DACHPt)). In this embodiment, the at least one primary hydroxyl group of the hyaluronic acid which has the modified histidine grafted thereto may comprise a hydroxyl group located on the fifth carbon atom of a N-acetyl-D-glucosamine of at least one disaccharide unit of the hyaluronic acid, but is not limited thereto. Furthermore, in this embodiment, a graft ratio of the Boc-histidine may be about 1-80%, a graft ratio of the $C_{11}H_{23}$ may be about 1-30%, and a weight ratio of the hyaluronic acid derivative to the active ingredient with a positive charge in water is about 2.5:1:1-4:1.

In addition, if the active ingredient with a positive charge in water contained in the biomedical composition of the present disclosure is a drug, the biomedical composition of the present disclosure may be a pharmaceutical composition or may be a drug delivery system.

The foregoing drug delivery system may be a micelle form, and the particle size of the micelle mentioned above may be about 100-1000 nm. In one embodiment, the particle size of the micelle mentioned above may be about 100-800 nm. In another embodiment, the particle size of the micelle mentioned above may be about 100-500 nm. In further another embodiment, the particle size of the micelle mentioned above may be about 100-300 nm.

The pharmaceutical composition may be administered orally, parenterally by an inhalation spray, or via an implanted reservoir. The parenteral method may comprise subcutaneous, intracutaneous, intravenous, intramuscular, intra-articular, intra-arterial, intrasynovial, intrasternal, intrathecal, and intralesional, as well as infusion techniques. For different administration manners, the pharmaceutical composition can be formulated into a dosage form by a conventional method.

An oral composition can comprise, but is not limited to, tablets, capsules, emulsions, and aqueous suspensions, dispersions and solutions.

Example

1. Preparation for a Hyaluronic Acid Derivative

A. Preparation for a Hyaluronic Acid Derivative Grafted with Boc-Histidine (HA-g-BocHis)

(a) Synthetical Mechanism of a Hyaluronic Acid Derivative Grafted with Boc-Histidine (HA-g-BocHis)

A synthetical mechanism of a hyaluronic acid derivative grafted with Boc-histidine (HA-g-BocHis) is shown as the following Formula (III):

Formula (III)

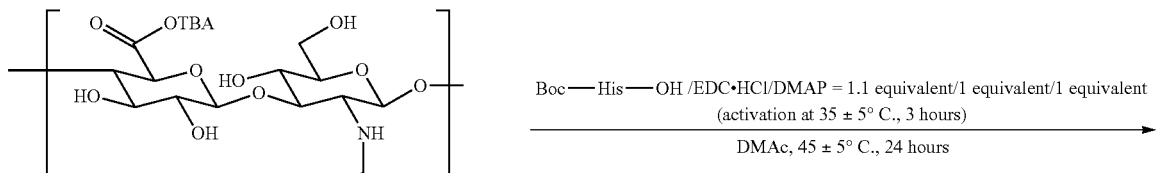

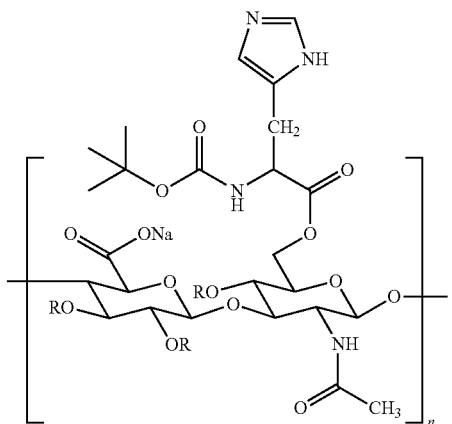

R = H or BocHis (b) Preparation Method of a Hyaluronic Acid Derivative Grafted with Boc-Histidine (HA-g-BocHis)

The preparation method of a hyaluronic acid derivative grafted with Boc-histidine (HA-g-BocHis) is described in the following:

(1) HA-TBA (1 equivalent, calculated by primary hydroxyl groups of the hyaluronic acid) was dried in vacuum at room temperature for 16 hours, weighted to take a needed amount and placed in a mezzanine-type glass reactive tank, and a mechanical stirring device was installed in the mezzanine-type glass reactive tank. After that, vacuum degasification was performed in the mezzanine-type glass reactive tank for 30 minutes.

(2) Nitrogen gas was backfilled into the mezzanine type glass reactive tank, and anhydrous DMAc (10 mL/g $HA_{16k}$-TBA) was also added in the mezzanine type glass reactive tank to form a mixture. Then, 45±5° C. recycling water was introduced into the mezzanine of the mezzanine-type glass reactive tank and the mixture was stirred at 250 rpm for 4 hours to be completely dissolved and ready for use.

(3) Boc-His-OH and DMAP were weighted to take a needed amount in a two-neck bottle. The two-neck bottle was vacuum pumped for 5 minutes, and then nitrogen gas was introduced therein. Then DMAc (0.5 M for Boc-His-OH) was added in the two-neck bottle and stirred well for 30 minutes, EDC.HCl solid was quickly poured into the two-neck bottle, and the reaction was performed at 35±5° C. for 4 hours to activate Boc-His-OH.

(4) The activated Boc-His-L (L=leaving group) solution was transferred into the mezzanine type glass reactive tank by a peristaltic pump with a flow rate of 25 mL/minute. After the feeding was completed, the rotation rate of the mechanical stirring device was raised to 300 rpm and the reaction was performed for 30 minutes to quickly mix the whole solution well, and then the rotation rate of the mechanical stirring device was decreased to 250 rpm and the reaction was continued for 24 hours.

(5) After the reaction naturally cooled down to room temperature, the solution was placed in a dialysis bag (Spectra/Por® 4 Dialysis Membrane, MWCO: 12-14,000, Flat Width: 75 mm).

(6) The dialysis bag was dialyzed with 45±5° C. DMAc (20×DMAc volume) continually for 40 hours, and the dialysis buffer was exchanged at the 16 hour point.

(7) The dialysis bag was transferred into 25±5° C. deionized water (100×DMAc volume) and dialyzed for 72 hours, continually, and the dialysis buffer was exchanged at the 2, 5, 8, 24, 26, 29, 32, 48, 50, 53 and 56 hour points.

(8) A glass chromatography column 60 cm in length and 5 cm in diameter was selected, and the bottom outlet of which was stoppered with glass wool. Sodium ion exchange resin (ROHM HAAS, food grade, 520 g) was well mixed with deionized water (200 mL) and then poured into the chromatography column. 200 mL deionized water was used to ash the resin in the chromatography column, and the washing was performed 5 or more times until the effluent liquid became transparent and colorless to complete the washing of the sodium ion exchange resin.

(9) The aqueous solution in the dialysis bag was collected and filtered with glass wool to remove the trace jellied solid. The filtrate was collected and passed through the sodium ion exchange resin with a flow rate of 150-200 mL/hour (the number of columns that were needed was calculated based on that one sodium ion exchange resin column, which only can be used to treat 15 g $HA_{16k}$-TBA). After the HA aqueous solution completely entered into the resin, the column was washed with deionized water 3 times to wash out the HA material remaining on the resin to obtain a HA-g-BocHis aqueous solution.

(10) The HA-g-BocHis aqueous solution was concentrated under vacuum (<1 mmHg, 30±5° C.) until an aqueous solution with a concentration of about 3 wt % was obtained. After a pH value for the solution was determined, the solution was placed at −20° C. to freeze.

(11) The water contained in the aqueous solution was removed through lyophilization to obtain a completely dry HA-g-BocHis material.

According to the preparation method described above, by adjusting the equivalent ratio of HA/Boc-His-OH/EDC.HCl/DMAP, HA-g-BocHis material with different BocHis graft ratios can be obtained. BocHis graft ratio and yield of HA-g-BocHis material with different BocHis graft ratios obtained through different equivalent ratios of HA/Boc-His-OH/EDC.HCl/DMAP are shown in Table 1.

TABLE 1

BocHis graft ratio and yield of HA-g-BocHis material with different BocHis graft ratio obtained through different equivalent ratio of HA/Boc-His-OH/EDC · HCl/DMAP

| Lot | BH/EDC · HCl/DMAP (equivalent) | BocHis graft ratio (1H-NMR) | Yield |
|---|---|---|---|
| 1 | 0.44/0.4/0.4 | 17% | 85% |
| 2 | 1.1/1/1 | 44% | 89% |
| 3 | 1.65/1.5/1.5 | 57% | 57% |
| 4 | 2.2/2/2 | 71% | 48% |
| 5 | 6.0/4/4 | 94% | 39% |

B. Preparation for a Hyaluronic Acid Derivative Grafted with Boc-Histidine and Polyethylene Glycol (PEG) (HA-g-(BocHis-co-SAmPEG))

(a) Synthetical Mechanism of a Hyaluronic Acid Derivative Grafted with Boc-Histidine and Polyethylene Glycol (PEG) (HA-g-(BocHis-co-SAmPEG))

A synthetical mechanism of a hyaluronic acid derivative grafted with Boc-histidine and polyethylene glycol (PEG) (HA-g-(BocHis-co-SAmPEG)) is shown as the following Formula (IV):

Formula (IV)

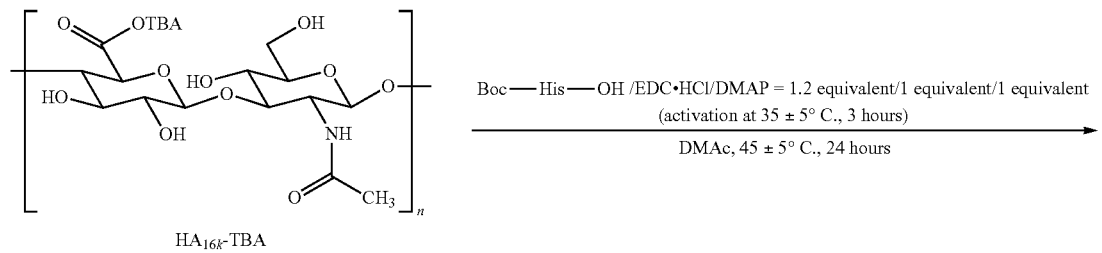

-continued mPEG$_{1900}$—SA—COOH/EDC·HCl/DMAP = 0.24 equivalent/0.2 equivalent/0.2 equivalent (activation at 35 ± 5° C., 3 hours)

DMAc, 45 ± 5° C., 40 hours

→ Dialysis
DMAc (20X), 35 ± 5° C., 40 hours
DIW (100X), 25 ± 5° C., 72 hours (1) Na+ exchange resin
(2) Remove water to dryness
(3) Soxhlet extraction with DCM for 6 hours (4) Re-dissolved in DIW (3 wt %)
(5) pH was adjusted to 7.6 ± 0.0
(6) Dried on a lyophilizer

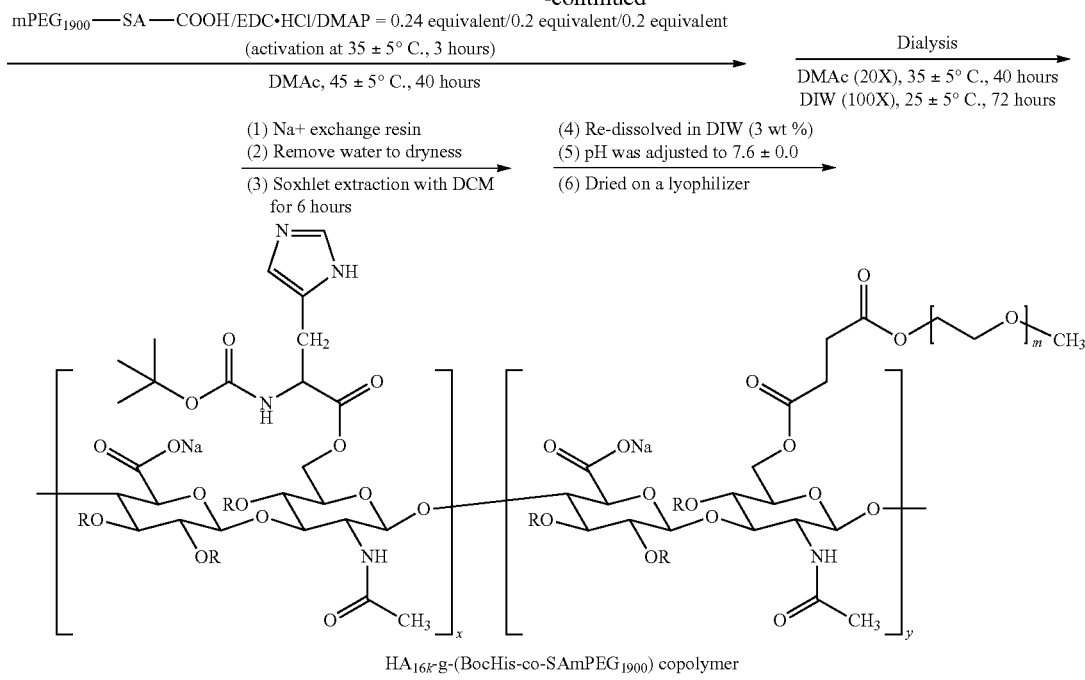

HA$_{16k}$-g-(BocHis-co-SAmPEG$_{1900}$) copolymer

R = H, BocHis or SAmPEG$_{1900}$ (b) Preparation Method of a Hyaluronic Acid Derivative Grafted with Boc-Histidine and Polyethylene Glycol (PEG) (HA-g-(BocHis-co-SAmPEG))

The Preparation method of a hyaluronic acid derivative grafted with Boc-histidine and polyethylene glycol (PEG) (HA-g-(BocHis-co-SAmPEG)) is described in the following:

(1) HA-TBA (1 equivalent, calculated by primary hydroxyl groups of the hyaluronic acid) was dried in vacuum at room temperature for 16 hours, weighted to take a needed amount and placed in a mezzanine-type glass reactive tank, and a mechanical stirring device was installed in the mezzanine-type glass reactive tank. After that, vacuum degasification was performed in the mezzanine-type glass reactive tank for 30 minutes.

(2) Nitrogen gas was backfilled into the mezzanine type glass reactive tank, and anhydrous DMAc (10 mL/g HA$_{16k}$-TBA) was also added in the mezzanine-type glass reactive tank to form a mixture. Then, 45±5° C. recycling water was introduced into the mezzanine of the mezzanine-type glass reactive tank and the mixture was stirred at 250 rpm for 4 hours to be completely dissolved and ready for use.

(3) Boc-His-OH and DMAP were weighted to take a needed amount in a two-neck bottle. The two-neck bottle was vacuum pumped for 5 minutes, and then nitrogen gas was introduced therein. Then DMAc (0.5 M for Boc-His-OH) was added in the two-neck bottle and stirred well for 30 minutes, EDC.HCl solid was quickly poured into the two-neck bottle, and the reaction was performed at 35±5° C. for 4 hours to activate Boc-His-OH.

(4) The activated Boc-His-L (L=leaving group) solution was transferred into the mezzanine-type glass reactive tank by a peristaltic pump with a flow rate of 1 mL/minute. After the feeding was completed, the rotation rate of the mechanical stirring device was raised to 300 rpm and the reaction was performed for 30 minutes to quickly mix the whole solution well, and then the rotation rate of the mechanical stirring device was decreased to 250 rpm and the reaction was continued for 24 hours.

(5) mPEG-SA-COOH were weighted to take a needed amount in a two-neck bottle. The two-neck bottle was vacuum pumped for 5 minutes, and then nitrogen gas was introduced therein. Then DMAc (0.1 M for mPEG1900-SA-COOH) was added in the two-neck bottle and well stirred at 50±5° C. for 10 minutes to uniformly dissolve mPEG-SA-COOH. After that the temperature was decreased to 30° C., and DMAP was added to the two-neck bottle and stirred for 10 minutes. Then EDC.HCl solid was quickly poured into the two-neck bottle, and the reaction was performed at 35±5° C. for 4 hours to activate mPEG-SA-COOH.

(6) The activated mPEG-SA-COL (L=leaving group) solution was transferred into the mezzanine-type glass reactive tank by a peristaltic pump with a flow rate of 1 mL/minute. After the feeding was completed, the rotation rate of the mechanical stirring device was raised to 300 rpm and the reaction was performed for 30 minutes to quickly mix the whole solution well, and then the rotation rate of the mechanical stirring device was decreased to 250 rpm and the reaction was continued for 24 hours.

(7) After the reaction naturally cooled down to room temperature, the solution was placed in a dialysis bag (Spectra/Por® 4 Dialysis Membrane, MWCO: 12-14,000, Flat Width: 75 mm).

(8) The dialysis bag was dialyzed with 45±5° C. DMAc (20×DMAc volume) continually for 40 hours, and the dialysis buffer was exchanged at the 16 hour point.

(9) The dialysis bag was transferred into 25±5° C. deionized water (100×DMAc volume) and dialyzed continually for 72 hours, and the dialysis buffer was exchanged at the 2, 5, 8, 24, 26, 29, 32, 48, 50, 53 and 56 hour points.

(10) A glass chromatography column 60 cm in length and 5 cm in diameter was selected, the bottom outlet of was stoppered with glass wool. Sodium ion exchange resin (ROHM HAAS, food grade, 520 g) was well mixed with deionized water (200 mL) and then poured into the chromatography column. 200 mL deionized water was used to ash the resin in the chromatography column, and the washing was performed than 5 or more times until the effluent liquid became transparent and colorless to complete the washing of the sodium ion exchange resin.

(11) The aqueous solution in the dialysis bag was collected and filtered with glass wool to remove the trace jellied solid. The filtrate was collected and passed through the sodium ion exchange resin with a flow rate of 150-200 mL/hour (the number of columns that were needed was calculated based on that one sodium ion exchange resin column, which only can be used to treat 15 g $HA_{16k}$-TBA). After the HA aqueous solution completely entered into the resin, the column was washed with deionized water 3 times to wash out the HA material remaining on the resin to obtain a HA-g-(BocHis-co-SAmPEG) aqueous solution.

(12) The HA-g-(BocHis-co-SAmPEG) aqueous solution was concentrated under vacuum (<1 mmHg, 30±5° C.) to completely dry. The solid product was weighted to take into a circular filter cartridge and washed with dichloromethane under a nitrogen atmosphere for 6 hours (recycled cooling water was 5° C.). After that, the solid was taken out and the remaining dichloromethane thereon was allowed to evaporate, to dry naturally. Deionized water was added to the solid to dissolve the solid to form an aqueous solution with a concentration of about 3 wt %. After a pH value for the solution was determined, the solution was placed at −20° C. to freeze.

(13) The water contained in the aqueous solution was removed through lyophilization to obtain a completely dry HA-g-(BocHis-co-SAmPEG).

According to the preparation method described above, by adjusting the equivalent ratios of HA/Boc-His-OH/EDC.HCl/DMAP and HA/mPEG-SA-COOH/EDC.HCl/DMAP, HA-g-(BocHis-co-SAmPEG) materials with different BocHis graft ratios and PEG graft ratios can be obtained. BocHis graft ratio, PEG graft ratio and yield of HA-g-(BocHis-co-SAmPEG) materials with different BocHis graft ratios and PEG graft ratios obtained through different equivalent ratios of HA/Boc-His-OH/EDC.HCl/DMAP and HA/mPEG-SA-COOH/EDC.HCl/DMAP are shown in Table 2.

TABLE 2

BocHis graft ratio, PEG graft ratio and yield of HA-g-(BocHis-co-SAmPEG) materials with different BocHis graft ratios and PEG graft ratios obtained by different equivalent ratios of HA/Boc-His-OH/ EDC · HCl/DMAP and HA/mPEG-SA-COOH/EDC · HCl/DMAP

| Lot | BH/EDC · HCl/DMAP (equivalent) | mPEG$_{1900}$-SA-COOH/ EDC · HCl/DMAP (equivalent) | Graft ratio (1H-NMR) BocHis | SAmPEG$_{1900}$ | Yield |
|---|---|---|---|---|---|
| 1$^a$ | 1.1/1/1 | 0.22/0.2/0.2 | 48% | 13% | 55% |
| 2$^a$ | 1.2/1/1 | 0.24/0.2/0.2 | 53% | 11% | 44% |
| 3$^a$ | 1.2/1/1 | 0.24/0.2/0.2 | 55% | 7% | 58% |
| 4$^b$ | 1.2/1/1 | 0.24/0.2/0.2 | 59% | 11% | 59% |
| 5$^b$ | 0.96/0.8/0.8 | 0.24/0.2/0.2 | 40% | 18% | 54% |
| 6$^b$ | 0.72/0.6/0.6 | 0.24/0.2/0.2 | 28% | 14% | 58% |
| 7$^b$ | 0.96/0.8/0.8 | 0.48/0.4/0.4 | 43% | 31% | 39% |
| 8$^b$ | 0.72/0.6/0.6 | 0.48/0.4/0.4 | 30% | 30% | 42% |

$^a$BocHis-L and mPEG1900-SA-COL were mixed with HA-TBA through a rapid feeding (25 mL/minute)
$^b$BocHis-L and mPEG1900-SA-COL were mixed with HA-TBA through a slow feeding (1 mL/minute)

C. Preparation for a Hyaluronic Acid Derivative Grafted with Boc-Histidine and $C_{11}H_{23}$ (HA-g-(BocHis-co-$C_{11}$))

(a) Synthetical Mechanism of a Hyaluronic Acid Derivative Grafted with Boc-Histidine and $C_{11}H_{23}$ (HA-g-(BocHis-co-$C_{11}$))

A synthetical mechanism of a hyaluronic acid derivative grafted with Boc-histidine and $C_{11}H_{23}$ (HA-g-(BocHis-co-$C_{11}$)) is shown as the following Formula (V):

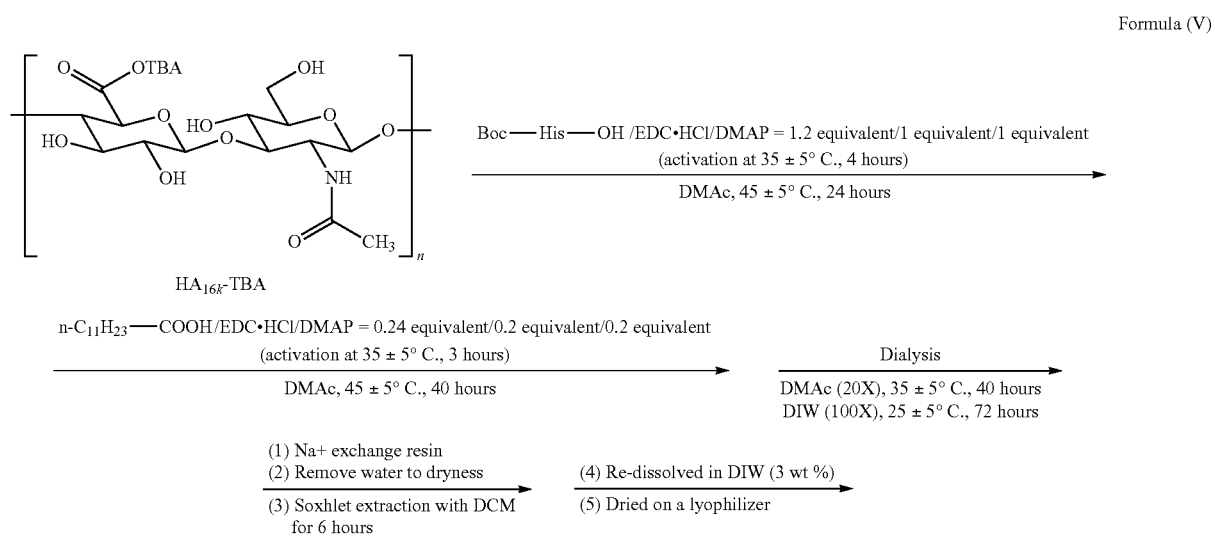

Formula (V)

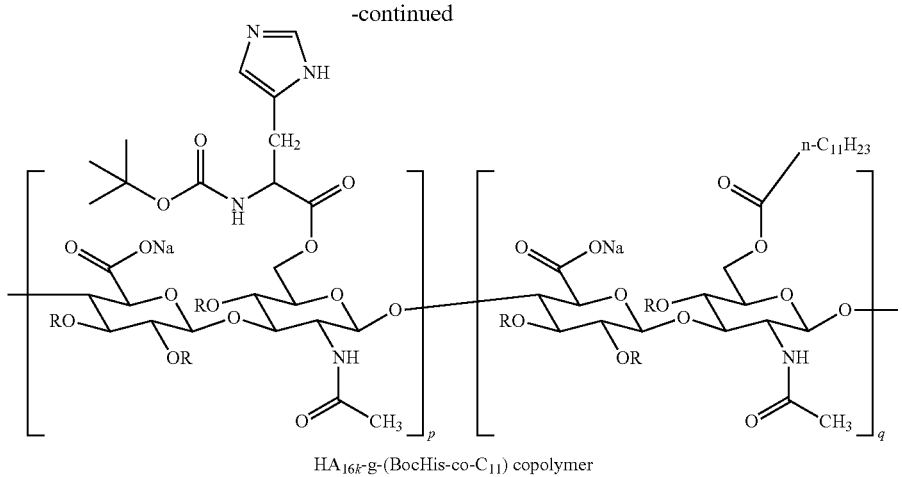

HA$_{16k}$-g-(BocHis-co-C$_{11}$) copolymer

R = H, BocHis or C$_{11}$ (b) Preparation Method of a Hyaluronic Acid Derivative Grafted with Boc-Histidine and C$_{11}$H$_{23}$ (HA-g-(BocHis-co-C$_{11}$))

The preparation method of a hyaluronic acid derivative grafted with Boc-histidine and C$_{11}$H$_{23}$ (HA-g-(BocHis-co-C$_{11}$)) is described in the following:

(1) HA-TBA (1 equivalent, calculated by primary hydroxyl groups of the hyaluronic acid) was dried in vacuum at room temperature for 16 hours, weighted to take a needed amount and placed in a mezzanine-type glass reactive tank, and a mechanical stirring device was installed in the mezzanine-type glass reactive tank. After that, vacuum degasification was performed in the mezzanine-type glass reactive tank for 30 minutes. (2) Nitrogen gas was backfilled into the mezzanine-type glass reactive tank, and anhydrous DMAc (10 mL/g HA$_{16k}$-TBA) was also added in the mezzanine-type glass reactive tank to form a mixture. Then, 45±5° C. recycling water was introduced into the mezzanine of the mezzanine-type glass reactive tank and the mixture was stirred at 250 rpm for 4 hours to be completely dissolved and ready for use.

(3) Boc-His-OH (1.1 equivalent) and DMAP (1 equivalent) were weighted to take a needed amount in a two-neck bottle. The two-neck bottle was vacuum pumped for 5 minutes, and then nitrogen gas was introduced therein. Then DMAc (0.5 M for Boc-His-OH) was added in the two-neck bottle and well stirred for 30 minutes, EDC.HCl solid (1 equivalent) was quickly poured into the two-neck bottle, and the reaction was performed at 35±5° C. for 4 hours to activate Boc-His-OH.

(4) The activated Boc-His-L (L=leaving group) solution was transferred into the mezzanine-type glass reactive tank by a peristaltic pump with a flow rate of 25 mL/minute. After the feeding was completed, the rotation rate of the mechanical stirring device was raised to 300 rpm and the reaction was performed for 30 minutes to quickly mix the whole solution well, and then the rotation rate of the mechanical stirring device was decreased to 250 rpm and the reaction was continued for 24 hours.

(5) n-C$_{11}$H$_{23}$—COOH (0.165 equivalent) and DMAP (0.15 equivalent) were weighted to take a needed amount in a two-neck bottle. The two-neck bottle was vacuum pumped for 5 minutes, and then nitrogen gas was introduced therein. Then DMAc (0.5 M for Boc-His-OH) was added in the two-neck bottle and well stirred for 30 minutes. Then, EDC.HCl solid (0.15 equivalent) was quickly poured into the two-neck bottle, and the reaction was performed at 35±5° C. for 4 hours to activate n-C$_{11}$H$_{23}$—COOH.

(6) The activated n-C$_{11}$H$_{23}$—COL (L=leaving group) solution was transferred into the mezzanine-type glass reactive tank by a peristaltic pump with a flow rate of 25 mL/minute. After the feeding was completed, the rotation rate of the mechanical stirring device was raised to 300 rpm and the reaction was performed for 30 minutes to quickly mix the whole solution well, and then the rotation rate of the mechanical stirring device was decreased to 250 rpm and the reaction was continued for 40 hours.

(7) After the reaction was naturally cool down to room temperature, the solution was placed in a dialysis bag (Spectra/Por® 4 Dialysis Membrane, MWCO: 12-14,000, Flat Width: 75 mm).

(8) The dialysis bag was dialyzed with 45±5° C. DMAc (20×DMAc volume) continually for 40 hours, and the dialysis buffer was exchanged at the 16 hour point.

(9) The dialysis bag was transferred into 25+5° C. deionized water (100×DMAc volume) and continually dialyzed for 72 hours, and the dialysis buffer was exchanged at the 2, 5, 8, 24, 26, 29, 32, 48, 50, 53 and 56 hour points.

(10) A glass chromatography column 60 cm in length and 5 cm in diameter was selected, the bottom outlet of which was stoppered with glass wool. Sodium ion exchange resin (ROHM HAAS, food grade, 520 g) was well mixed with deionized water (200 mL) and then poured into the chromatography column. 200 mL deionized water was used to ash the resin in the chromatography column, and the washing was performed 5 or more times until the effluent liquid became transparent and colorless to complete the washing of the sodium ion exchange resin.

(11) The aqueous solution in the dialysis bag was collected and filtered with glass wool to remove the trace jellied solid. The filtrate was collected and passed through the sodium ion exchange resin with a flow rate of 150-200 mL/hour (the number of the columns that were needed was calculated based on that one sodium ion exchange resin column, which only can be used to treat 15 g HA$_{16k}$-TBA). After the HA aqueous solution completely entered into the resin, the column was washed with deionized water 3 times to wash out the HA material remaining on the resin to obtain a HA-g-(BocHis-co-$C_{11}$) aqueous solution.

(12) The HA-g-(BocHis-co-$C_{11}$) aqueous solution was concentrated under vacuum (<1 mmHg, 30±5° C.) until an aqueous solution with a concentration of about 3 wt % was obtained. After a pH value for the solution was determined, the solution was placed at −20° C. to freeze.

(13) The water contained by the aqueous solution was removed through lyophilization to obtain a completely dry HA-g-(BocHis-co-$C_{11}$), and the yield of the HA-g-(BocHis-co-$C_{11}$) was 62%.

2. Analysis for pH-Responsive Property of Histidine-Based HA

A. Critical Micelle Concentration (CMC)

When concentration of a material is higher than critical micelle concentration, the material will form micelles. Since pyrene has the property of being susceptible to the change of hydrophilicity/hydrophobicity in a micro-environment, when a micelle material has a concentration that is higher than the critical micelle concentration thereof, intensity of emitted fluorescent light from the pyrene will increase rapidly. In this example, according to the property of the pyrene mentioned above, the critical micelle concentration of the micelle material was determined. The testing methods are described in the following:

Each test sample was formulated into a 1 mg/mL aqueous solution, and then each sample was formulated into 4.5 mL of aqueous solution at the following concentrations through 2× dilution based on the 1 mg/mL aqueous solution. The concentrations mentioned above, from lowest to highest, were (1) 0.00195 mg/mL; (2) 0.00391 mg/mL; (3) 0.00781 mg/mL; (4) 0.01563 mg/mL; (5) 0.03125 mg/mL; (6) 0.0625 mg/mL; (7) 0.125 mg/mL; (8) 0.25 mg/mL; (9) 0.5 mg/mL; and (10) 1 mg/mL. Then 15 μl of $1.8 \times 10^{-4}$ M pyrene acetone solution was added to the ten sample solutions, mixed well, and then allowed to stand until the next day. After that, the sample solutions were vacuum pumped at room temperature for 20 minutes to allow the acetone to evaporate. After that, the intensity of emitted fluorescent light from the pyrene was measured to determine the critical micelle concentration of the test sample.

For a determination of fluorescent intensity, an excitation wavelength was set at 339 nm and an emission wavelength at 360-500 nm, and intensity of emission light at maximum emission wavelength $I_{max}$ (namely, $I_{379\ nm}$) was plotted against log value of material concentration to obtain the critical micelle concentration of the material.

(1) Critical Micelle Concentration of the Hyaluronic Acid Derivative Grafted with Boc-Histidine The critical micelle concentration of the hyaluronic acid derivative grafted with Boc-histidine obtained above, $HA_{16k}$-g-40% BocHis material, was determined through the method described above.

Figure 1B:
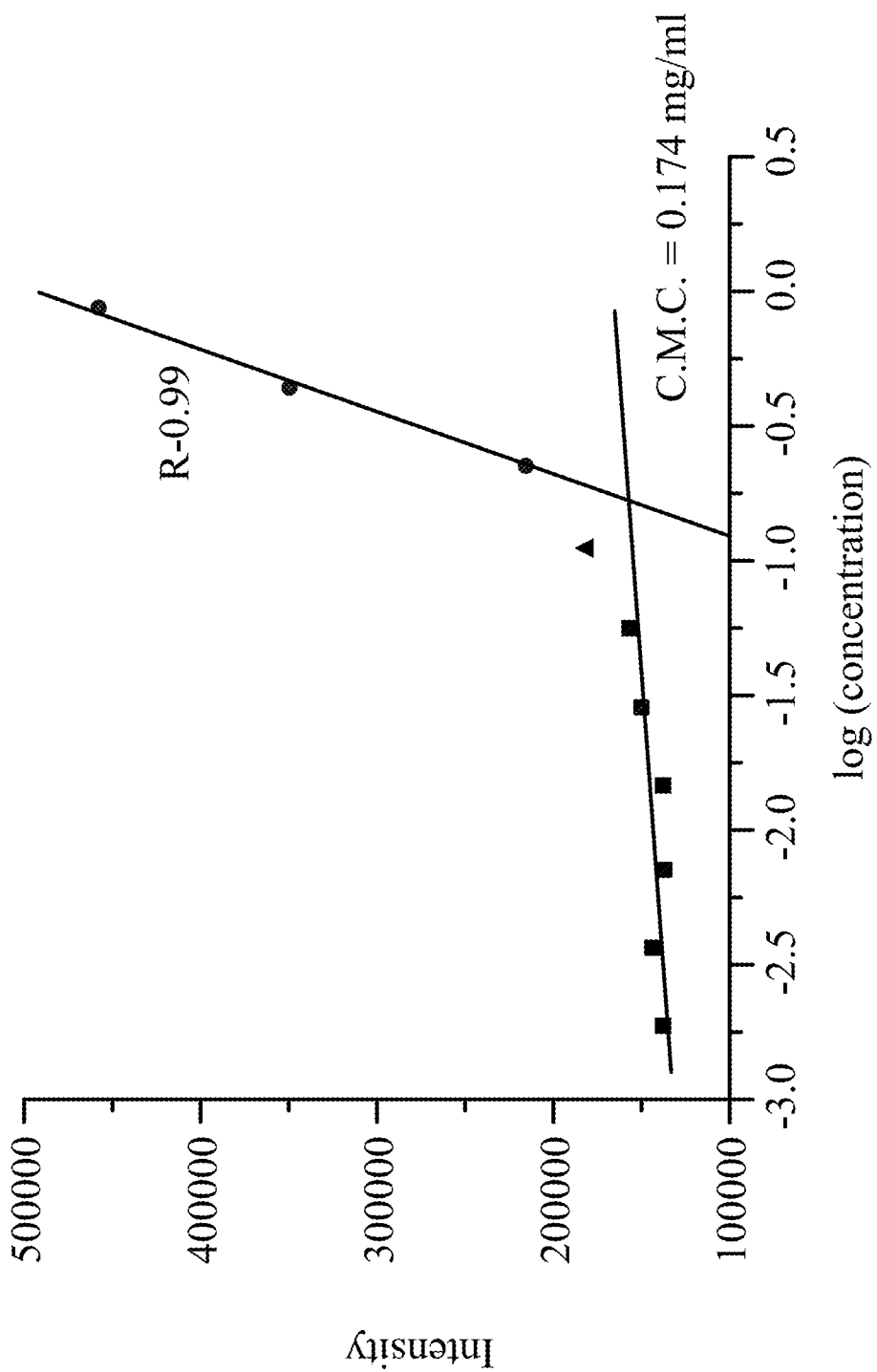
FIG. 1B shows the result of determining the critical micelle concentrations of the $HA_{16k}$-g-40% BocHis material at pH 5 according to an exemplary embodiment.

The result showed that hydrophobicity of Boc-histidine provides a possibility for the material to form micelles in an aqueous solution. In addition, critical micelle concentrations of the $HA_{16k}$-g-40% BocHis material at pH 8.0, 7.4, 6.5, 6.0 and 5.0 were 0.11, 0.10, 0.10, 0.11 and 0.18 mg/mL (n=2), respectively (see Table 3). Furthermore, the foregoing result shows that the micelle structure of the $HA_{16k}$-g-40% BocHis material is unstable in an acidic environment. The results of determining the critical micelle concentrations of the $HA_{16k}$-g-40% BocHis material at pH 7.4 and 5 are shown in FIG. 1A and FIG. 1B, respectively.

TABLE 3

Critical micelle concentrations of the $HA_{16k}$-g-40%BocHis material in different pH environments.

| pH | Critical micelle concentration (mg/mL) |
|---|---|
| 8.0 | 0.11 ± 0.01 |
| 7.4 | 0.10 ± 0.01 |
| 6.5 | 0.10 ± 0.01 |
| 6.0 | 0.11 ± 0.01 |
| 5.0 | 0.18 ± 0.01 |

(2) Critical Micelle Concentration of the Hyaluronic Acid Derivative Grafted with Boc-Histidine and $C_{11}H_{23}$ The critical micelle concentration of the hyaluronic acid derivative grafted with Boc-histidine and $C_{11}H_{23}$ obtained above, $HA_{16k}$-g-(45% BocHis-co-12% $C_{11}$) material, was determined through the method mentioned above.

Figure 2A:
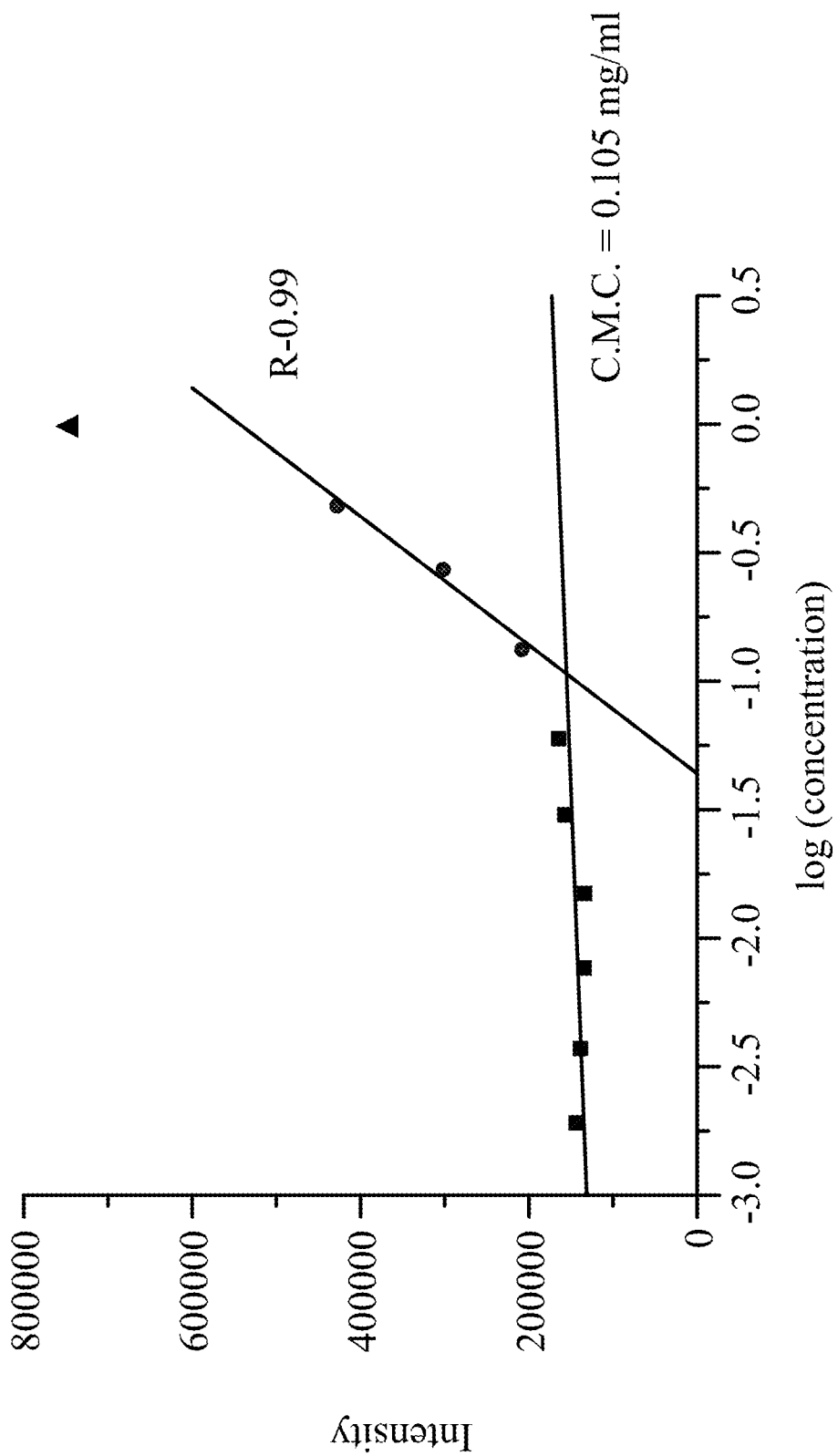
FIG. 2A shows the result of determining the critical micelle concentrations of the $HA_{16k}$-g-(45% BocHis-co-12% $C_{11}$) material at pH 7.4 according to an exemplary embodiment.
Figure 2B:
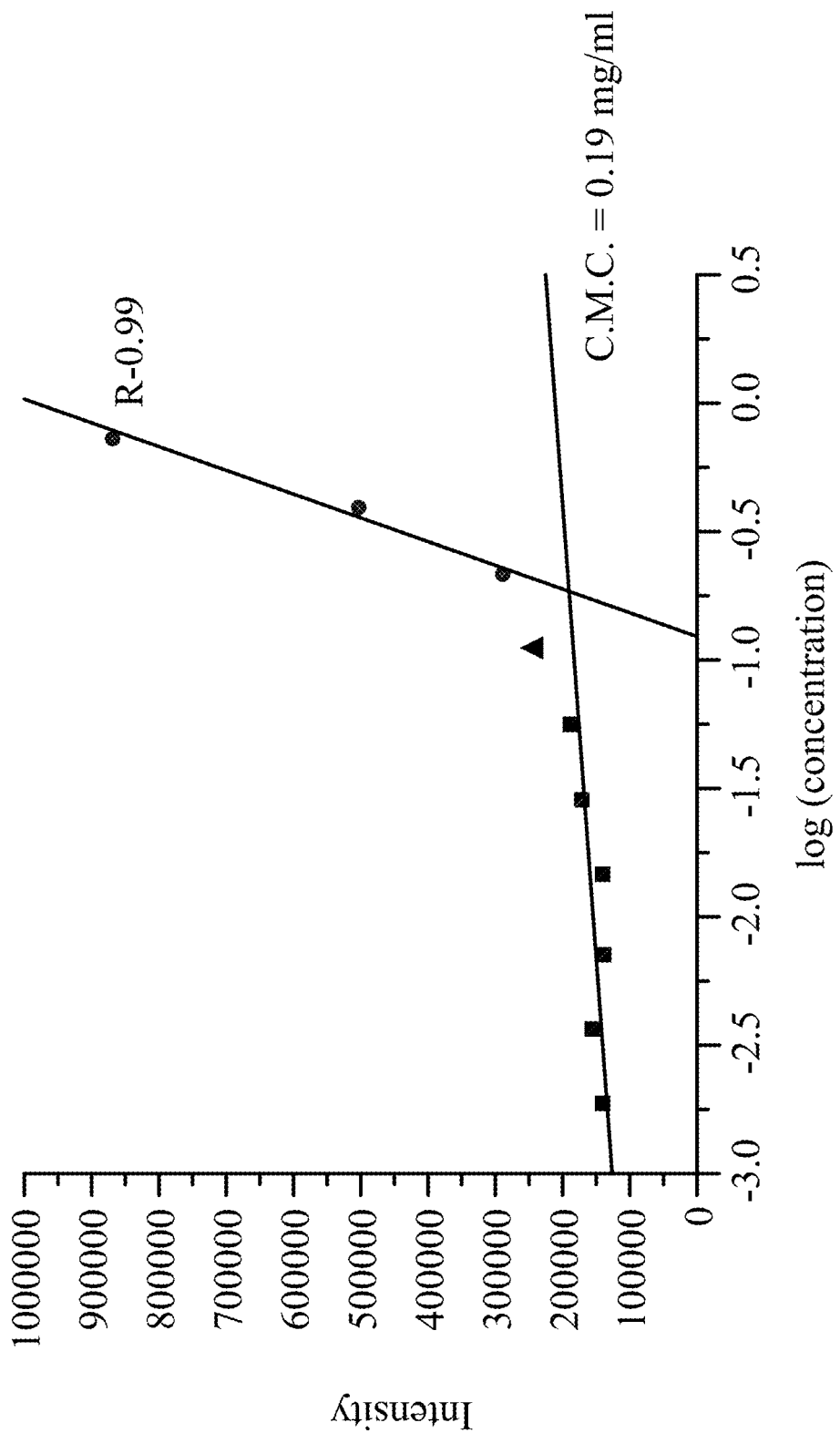
FIG. 2B shows the result of determining the critical micelle concentrations of the $HA_{16k}$-g-(45% BocHis-co-12% $C_{11}$) material at pH 5 according to an exemplary embodiment.

Critical micelle concentration of the $HA_{16k}$-g-(45% BocHis-co-12% $C_{11}$) material at pH 7.4 and 5.0 were 0.12 and 0.18 mg/mL, respectively (see Table 4). Furthermore, the foregoing result showed that the micelle structure of the $HA_{16k}$-g-(45% BocHis-co-12% $C_{11}$) material is unstable in an acid environment, and that is consistent with the preceding result. The results of determining the critical micelle concentrations of the $HA_{16k}$-g-(45% BocHis-co-12% $C_{11}$) material at pH 7.4 and 5 are shown in FIG. 2A and FIG. 2B, respectively.

TABLE 4

Critical micelle concentrations of $HA_{16k}$-g-(45%BocHis-co-12%$C_{11}$) material in different pH environments.

| pH | Critical micelle concentration (mg/mL) |
|---|---|
| 7.4 | 0.12 ± 0.01 |
| 5.0 | 0.18 ± 0.01 |

B. Particle Size of Micelle

The $HA_{16k}$-g-40% BocHis material was dissolved in PBS buffers of pH 8, pH 7.4, pH 6.5, pH 6 and pH 5. Next, pyrene was added to the above-mentioned PBS buffers containing the $HA_{16k}$-g-40% BocHis material, respectively, mixed well, and then allowed to stand. After that, the obtained solutions were filtered through a 0.45 μm filtering membrane and allowed to stand for 3 hours. Then, the particle size of micelle in the solution at each pH value was determined by a laser scattering particle size distribution analyzer. The results are shown in FIG. 3.

Figure 3:
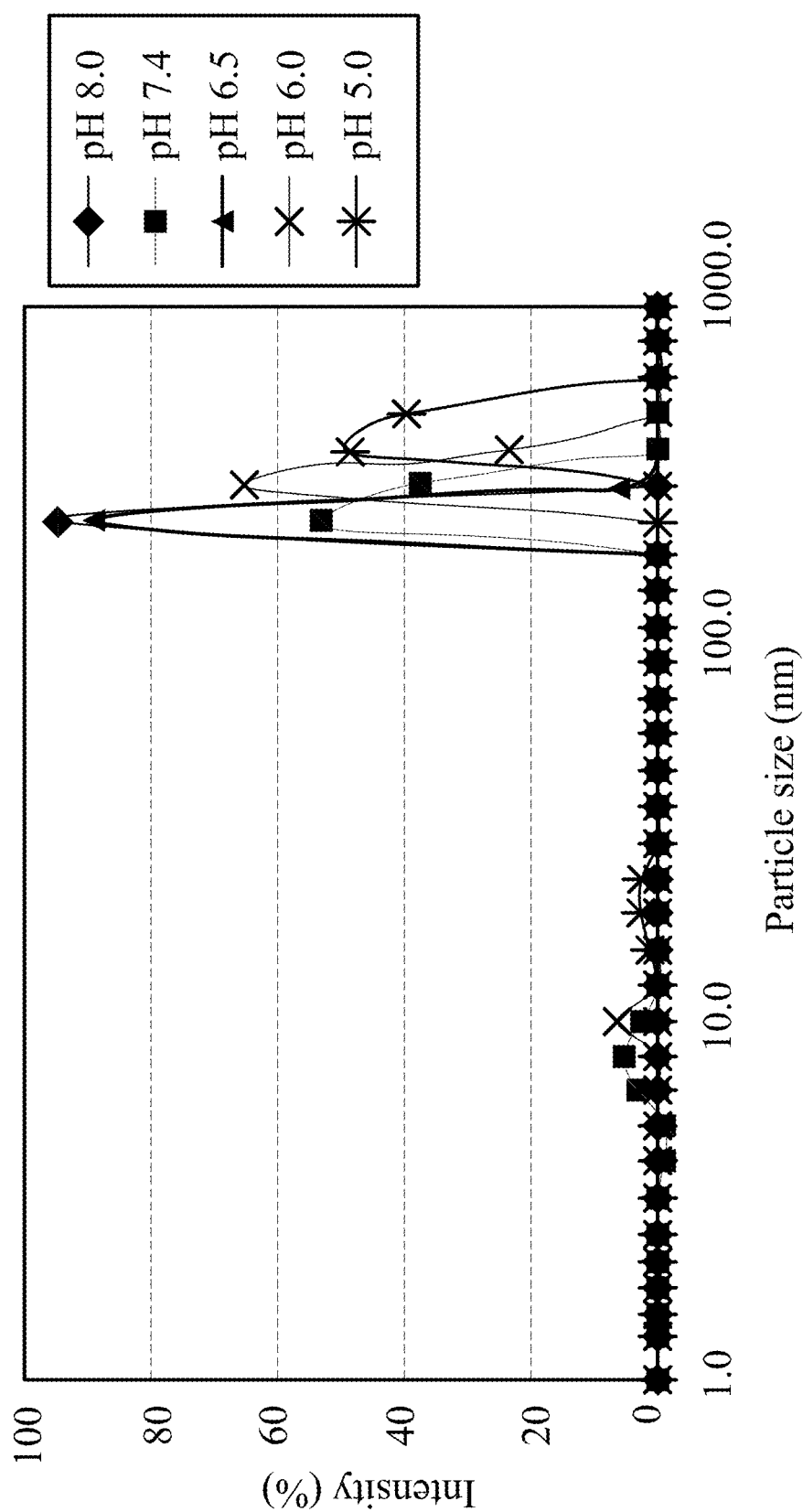
FIG. 3 shows the results of determining the particle size of micelle formed by $HA_{16k}$-g-40% BocHis material at pH 8, pH 7.4, pH 6.5, pH 6 and pH 5 by a laser scattering particle size distribution analyzer according to an exemplary embodiment.

According to FIG. 3, it is known that when pH value decreases from pH 8.0 to pH 6.0, the particle size of the micelles formed increases progressively.

C. pKa Potentiometric Titration

Figure 4:
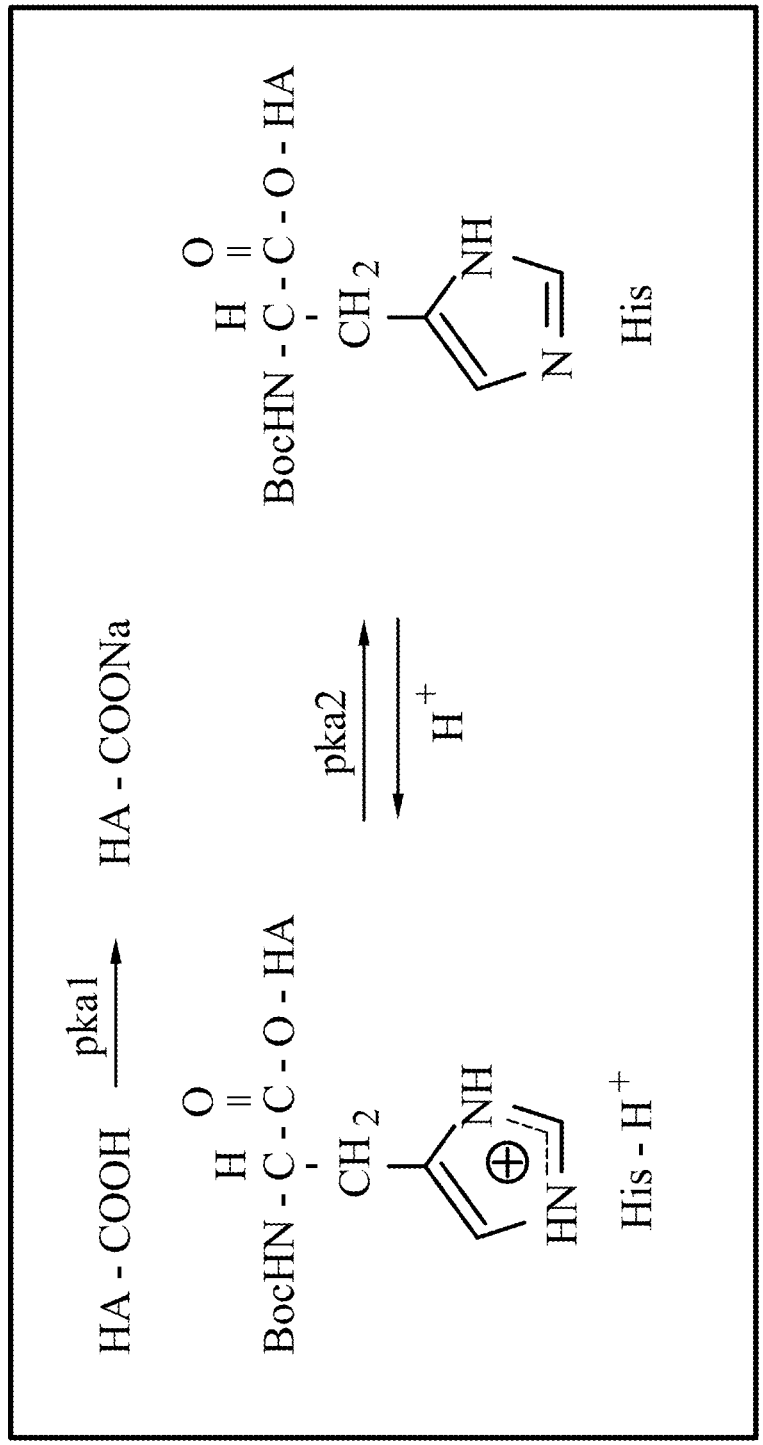
FIG. 4 shows a theoretical dissociation equation for the hyaluronic acid derivative of the present disclosure according to an exemplary embodiment.

Theoretical dissociation equation for the hyaluronic acid derivative of the present disclosure is shown in FIG. 4. pKa potentiometric titration was performed to HA-g-BocHis material and HA-g-(BocHis-co-SAmPEG) material with different respective graft ratios, and the results are show in Table 5.

TABLE 5

Results of performing pKa potentiometric titration to HA-g-BocHis material and HA-g-(BocHis-co-SAmPEG) material with different graft ratios

| Sample | pKa1 (HA-COOH) | pKa2 (His) |
|---|---|---|
| $HA_{16k}$-g-17%BocHis | 3.61 ± 0.01 | 7.15 ± 0.08 |
| $HA_{16k}$-g-40%BocHis | 3.59 ± 0.01 | 7.17 ± 0.09 |
| $HA_{16k}$-g-71%BocHis | 3.56 ± 0.01 | 7.22 ± 0.13 |
| $HA_{16k}$-g-(40%BocHis-co-10%SAmPEG$_{5k}$) | 3.59 ± 0.01 | 6.93 ± 0.06 |
| $HA_{16k}$-g-(48%BocHis-co-13%SAmPEG$_{1900}$) | 3.68 ± 0.04 | 7.26 ± 0.03 |

According to Table 5, it is known that HA-g-BocHis material and HA-g-(BocHis-co-SAmPEG) material both have two pKa values, wherein one is pKa1 of HA-COOH and the other is pKa 2 of histidine, and that explains that at pH 2.5-4.5 and at pH 6-8, the charge property of the materials will change due to protonation or deprotonation.

3. Preparation of Hyaluronic Acid Derivative/Drug Complex Nano-Carrier

Hyaluronic acid derivative and a drug solution (doxorubicin, irinotecan, gentamicin or dichloro(1,2-diaminocyclohexane)platinum (DACHPt)) were stirred by a stir bar to react with each other for 4-72 hours to form a mixture and package the drug in the hyaluronic acid derivative to form a hyaluronic acid derivative/drug complex nano-carrier. The above-mentioned mixture was poured in a MWCO 3,500 dialysis bag and dialyzed with water for 24 hours to remove the drug which is not packaged by the hyaluronic acid derivative, and particle size and formulation of hyaluronic acid derivative/drug complex nano-carrier formed in the solution obtained thereby were analyzed.

Formulations of hyaluronic acid derivative/drug complex nano-carriers formed by different hyaluronic acid derivatives and doxorubicin are shown in Table 6, formulations of hyaluronic acid derivative/drug complex nano-carriers formed by different hyaluronic acid derivatives and irinotecan are shown in Table 7, formulations of hyaluronic acid derivative/drug complex nano-carriers formed by different hyaluronic acid derivatives and gentamicin are shown in Table 8, and formulations of hyaluronic acid derivative/drug complex nano-carriers formed by different hyaluronic acid derivatives and dichloro(1,2-diaminocyclohexane)platinum (DACHPt) are shown in Table 9.

TABLE 6

Formulations of hyaluronic acid derivative/drug complex nano-carriers formed by different hyaluronic acid derivatives and doxorubicin

| Number of formulation | Hyaluronic acid derivative | Hyaluronic acid derivative wt (%) | Doxorubicin wt (%) | Particle size (nm) |
|---|---|---|---|---|
| DHC1902 | $HA_{16k}$-g-49%BocHis | 0.5 | 0.15 | 265.8 |
| DHC2101 | $HA_{16k}$-g-(48%BocHis-co-13%SAmPEG$_{1900}$) | 0.5 | 0.15 | 289.9 |
| DHC2102 | $HA_{16k}$-g-(48%BocHis-co-13%SAmPEG$_{1900}$) | 0.5 | 0.1 | 222 |
| DHC2103 | $HA_{16k}$-g-(48%BocHis-co-13%SAmPEG$_{1900}$) | 0.5 | 0.05 | 368.1 |
| DHC2104 | $HA_{16k}$-g-(48%BocHis-co-13%SAmPEG$_{1900}$) | 1 | 0.15 | 271.7 |
| DHC2105 | $HA_{16k}$-g-(48%BocHis-co-13%SAmPEG$_{1900}$) | 1.5 | 0.15 | 790.7 |
| DHC2301 | $HA_{16k}$-g-74%Histidine | 0.5 | 0.15 | 266.8 |
| DHC2302 | $HA_{16k}$-g-74%Histidine | 0.6 | 0.15 | 276.6 |
| DHC2303 | $HA_{16k}$-g-74%Histidine | 0.7 | 0.15 | 294.5 |
| DHC2501 | $HA_{16k}$-g-44%Histidine | 0.5 | 0.15 | 342.2 |
| DHC2502 | $HA_{16k}$-g-44%Histidine | 1 | 0.15 | 370.6 |
| DHC2504 | $HA_{16k}$-g-44%Histidine | 0.4 | 0.15 | 370.5 |
| DHC2505 | $HA_{16k}$-g-44%Histidine | 0.3 | 0.15 | 524 |
| DHC2506 | $HA_{16k}$-g-44%Histidine | 0.2 | 0.15 | 沈澱 |
| DHC2701 | $HA_{16k}$-g-(12%C$_{11}$-co45%Histidine) | 0.5 | 0.15 | 433.5 |
| DHC2702 | $HA_{16k}$-g-(12%C$_{11}$-co45%Histidine) | 0.6 | 0.15 | 302.2 |
| DHC2703 | $HA_{16k}$-g-(12%C$_{11}$-co45%Histidine) | 0.4 | 0.15 | 318.1 |

TABLE 7

Formulations of hyaluronic acid derivative/drug complex nano-carriers formed by different hyaluronic acid derivatives and irinotecan

| Number of formulation | Hyaluronic acid derivative | Hyaluronic acid derivative wt (%) | Irinotecan wt (%) | Particle size (nm) |
|---|---|---|---|---|
| IHC001 | $HA_{16k}$-g-(48%BocHis-co-13%SAmPEG1900) | 0.5 | 0.02 | 781.3 |
| IHC003 | $HA_{16k}$-g-(48%BocHis-co-13%SAmPEG1900) | 0.5 | 0.05 | 640.6 |
| IHC005 | $HA_{16k}$-g-(48%BocHis-co-13%SAmPEG1900) | 0.5 | 0.1 | 422.9 |
| IHC002 | $HA_{16k}$-g-44%Histidine | 0.5 | 0.03 | 659.9 |
| IHC004 | $HA_{16k}$-g-44%Histidine | 0.5 | 0.08 | 596.7 |
| IHC006 | $HA_{16k}$-g-44%Histidine | 0.5 | 0.16 | 449.7 |

TABLE 8

Formulations of hyaluronic acid derivative/drug complex nano-carriers formed by different hyaluronic acid derivatives and gentamicin

| Number of formulation | Hyaluronic acid derivative | Hyaluronic acid derivative wt (%) | Gentamicin wt (%) | Particle size (nm) |
|---|---|---|---|---|
| GHC001 | $HA_{16k}$-g-(48%BocHis-co-13%SAmPEG$_{1900}$) | 0.5 | 0.01 | 427.9 |
| GHC003 | $HA_{16k}$-g-(48%BocHis-co-13%SAmPEG$_{1900}$) | 0.5 | 0.03 | 372.2 |
| GHC005 | $HA_{16k}$-g-(48%BocHis-co-13%SAmPEG$_{1900}$) | 0.5 | 0.09 | 325.3 |
| GHC002 | $HA_{16k}$-g-44%Histidine | 0.5 | 0.02 | 350.1 |
| GHC004 | $HA_{16k}$-g-44%Histidine | 0.5 | 0.05 | 388.7 |
| GHC006 | $HA_{16k}$-g-44%Histidine | 0.5 | 0.15 | 237.0 |

TABLE 9

Formulations of hyaluronic acid derivative/drug complex nano-carriers formed by different hyaluronic acid derivatives and dichloro(1,2-diaminocyclohexane) platinum (DACHPt)

| Number of formulation | Hyaluronic acid derivative | Hyaluronic acid derivative wt (%) | dichloro(1,2-diamino-cyclohexane) platinum (DACHPt) wt (%) | Particle size (nm) |
|---|---|---|---|---|
| PtHC101 | $HA_{16k}$ | 1.2 | 0.4 | 281.7 |
| PtHC201 | $HA_{16k}$-g-17%Histidine | 1.2 | 0.4 | 179.1 |
| PtHC203 | $HA_{16k}$-g-17%Histidine | 1.3 | 0.4 | 163.5 |
| PtHC301 | $HA_{16k}$-g-44%Histidine | 1.2 | 0.4 | 129.8 |
| PtHC303 | $HA_{16k}$-g-44%Histidine | 0.5 | 0.4 | 112.9 |
| PtHC304 | $HA_{16k}$-g-44%Histidine | 0.9 | 0.4 | 144.7 |
| PtHC305 | $HA_{16k}$-g-44%Histidine | 1.4 | 0.4 | 162.0 |
| PtHC306 | $HA_{16k}$-g-44%Histidine | 1.9 | 0.4 | 193.7 |
| PtHC310 | $HA_{16k}$-g-44%Histidine | 0.7 | 0.2 | 149.4 |
| PtHC401 | $HA_{16k}$-g-71%Histidine | 1.2 | 0.4 | 160.2 |
| PtHC403 | $HA_{16k}$-g-71%Histidine | 1.5 | 0.4 | 174.5 |
| PtHC603 | $HA_{16k}$-g-(48%BocHis-co-13%SAmPEG$_{1900}$) | 2.2 | 0.4 | 203.6 |
| PtHC604 | $HA_{16k}$-g-(48%BocHis-co-13%SAmPEG$_{1900}$) | 1.1 | 0.2 | 116.4 |
| PtHC607 | $HA_{16k}$-g-(48%BocHis-co-13%SAmPEG$_{1900}$) | 1.4 | 0.2 | 100.9 |
| PtHC609 | $HA_{16k}$-g-(48%BocHis-co-13%SAmPEG$_{1900}$) | 1.8 | 0.2 | 115.7 |
| PtHC1401 | $HA_{16k}$-g-94%Histidine | 0.9 | 0.2 | 165.8 |
| PtHC1402 | $HA_{16k}$-g-94%Histidine | 0.6 | 0.2 | precipitate |
| PtHC1403 | $HA_{16k}$-g-94%Histidine | 1.2 | 0.2 | 155.4 |
| PtHC1501 | $HA_{16k}$-g-(40%BocHis-co-10%SAmPEG$_{5000}$) | 1.4 | 0.2 | 207.3 |
| PtHC1502 | $HA_{16k}$-g-(40%BocHis-co-10%SAmPEG$_{5000}$) | 1.9 | 0.2 | 214.1 |

4. Property Analysis for Hyaluronic Acid Derivative/Drug Complex Nano-Carriers (1) a. Hyaluronic Acid Derivative/Doxorubicin Complex Nano-Carrier Transmission Electron Microscopy (TEM)

Figure 5:
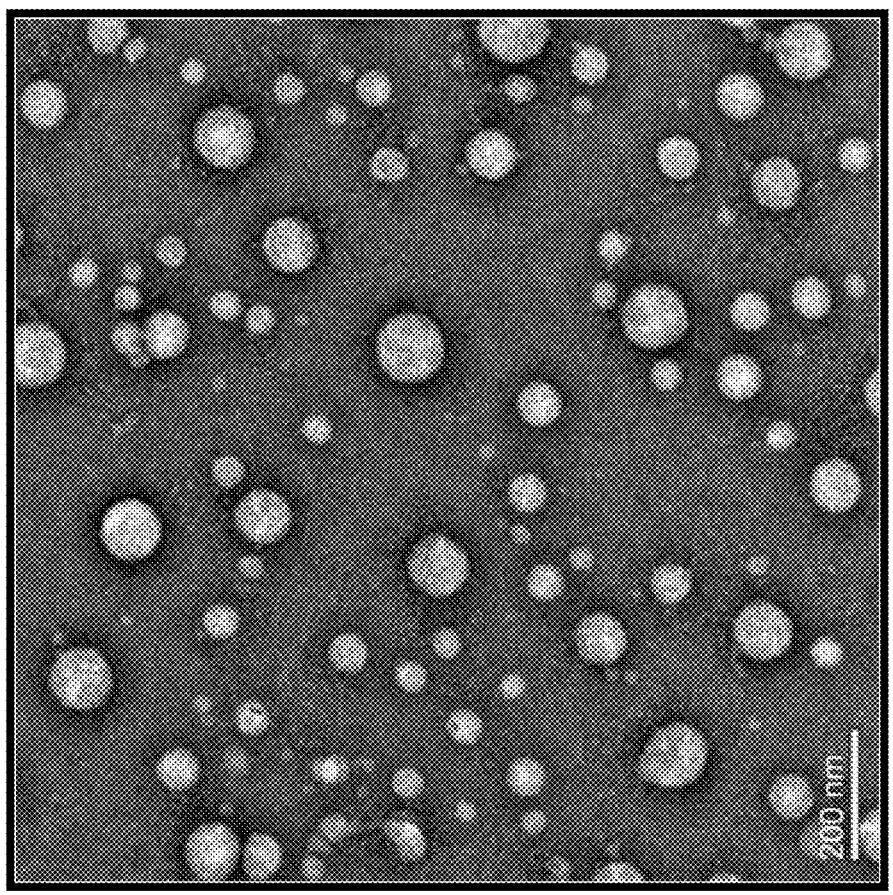
FIG. 5 shows a transmission electron microscope photograph of hyaluronic acid derivative/doxorubicin complex nano-carrier (formulation number DHC1902) according to an exemplary embodiment.

A hyaluronic acid derivative/doxorubicin complex nano-carrier (formulation number DHC1902) was observed and photographed by a transmission electron microscope, and the result is shown in FIG. 5.

According to FIG. 5, it is understood that the hyaluronic acid derivative is capable of forming a micelle.

(2) Effect of pH Value on Drug Release

Figure 6:
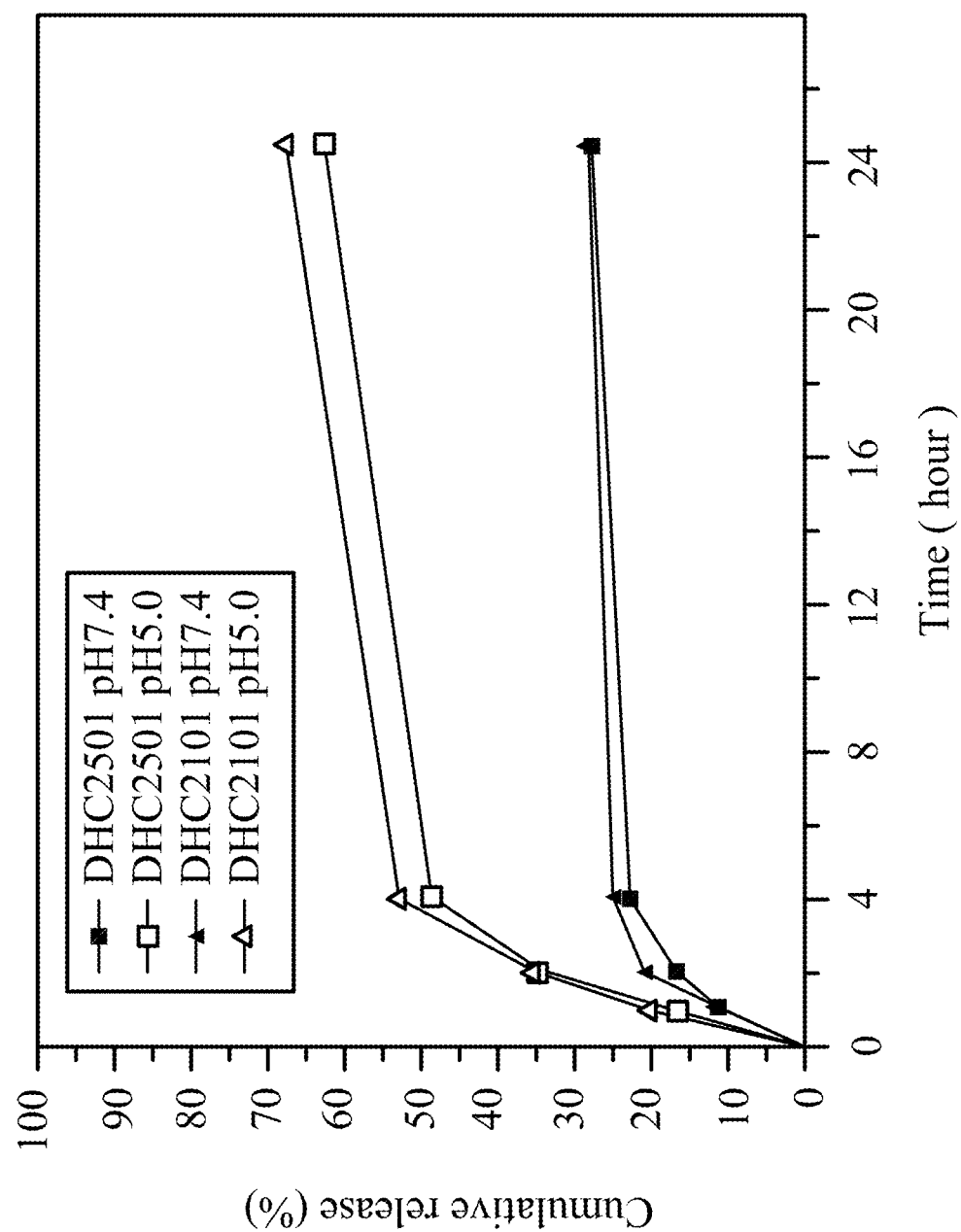
FIG. 6 shows the results of performing cumulative drug release analysis to hyaluronic acid derivative/doxorubicin complex nano-carriers formed by formulation numbers DHC2101 and DHC2501, respectively at pH 7.4 and pH 5.0 according to an exemplary embodiment.

Cumulative drug release analysis was performed on hyaluronic acid derivative/doxorubicin complex nano-carriers formed by formulation numbers DHC2101 and DHC2501, respectively at pH 7.4 and pH 5.0, and the results are shown in FIG. 6. Details of the experimental method for the cumulative drug release analysis are described in the following.

500 µL of the formulation was placed in a dialysis bag (MWCO 3.5 kD). Next, the two openings of the dialysis bag were fixed by dialysis clamps, and the dialysis bag was placed in a bottle, and then a dialysis external solution was introduced into the bottle. The dialysis external solution was 15 mL of PBS with different pH values (pH 7.4 or pH 5.0). The sample bottle was placed in a thermostatic shaker incubator at 37° C. to perform drug release, and the dialysis external solution was sampled at each sampling time point and the amount of drug release at excitation wavelength 500 nm/emission wavelength 560 nm was determined.

According to FIG. 6, it is known that as compared with a level of pH 7.4, hyaluronic acid derivative/doxorubicin complex nano-carriers respectively formed by Formulation DHC2101 and Formulation DHC2501 both have higher cumulative drug release rates at pH 5.0 (greater than 2.5 fold).

(3) Cytotoxicity Analysis

Figure 7:
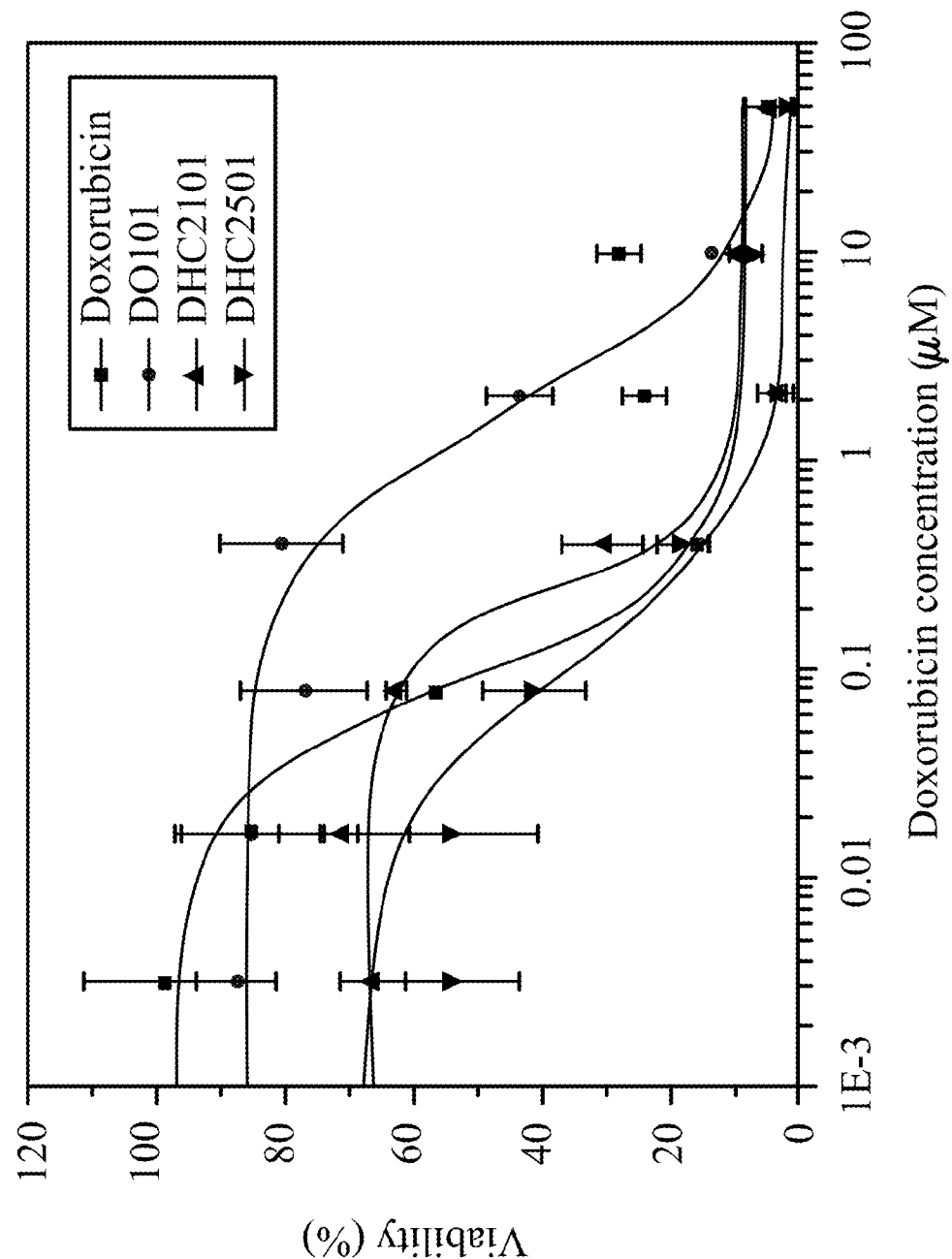
FIG. 7 shows the results of performing cytotoxicity analyses of hyaluronic acid derivative/doxorubicin complex nano-carriers respectively formed by Formulation DHC2101 and Formulation DHC2501, doxorubicin and doxorubicin packaged by liposome (DO101) through U87MC cells according to an exemplary embodiment.

A cytotoxicity analysis was performed on hyaluronic acid derivative/doxorubicin complex nano-carriers respectively formed by Formulation DHC2101 and Formulation DHC2501, doxorubicin and doxorubicin packaged by liposome (DO101) through U87MC cells, and $IC_{50}$ of hyaluronic acid derivative/doxorubicin complex nano-carriers respectively formed by Formulation DHC2101 and Formulation DHC2501, doxorubicin and doxorubicin packaged by liposome (DO101) were calculated, respectively. The results are shown in FIG. 7 and Table 10. Details of the experimental method for the cytotoxicity analysis are described in the following.

U87 cells were inoculated in a 96-well culture plate with a density of $1 \times 10^4$ cells/well, and cultured in a 37° C., 5% $CO_2$ incubator for 1 day. After that, the old culturing medium was remove from the culture plate, and 100 µL of 50 µM, 10 µM, 2 µM, 0.4 µM, 80 nM, 16 nM and 3.2 nM doxorubicin, DO101, DHC2101 or DHC2501 were added to the culture plate, respectively, to react for 48 hours. Next, the old medium was removed from the culture plate and the culture plate was washed with medium three times. After the medium was removed from the culture plate, 100 µL of 0.5 mg/mL MTT reagent was added to the plate, and the culture plate was incubated at 37° C. for 4 hours. Then, the old medium was removed and 100 µL of 0.1 N HCl/isopropanol was added to the culture plate to dissolve the precipitate. Finally, the culture plate was placed in a ELISA reader to determine the absorbance at wavelength 570 nm, and the absorbance was converted into cell viability based on the following formula:

Cell viability (%)=Intensity of sample/Intensity of control×100%.

TABLE 10

$IC_{50}$ of hyaluronic acid derivative/doxorubicin complex nano-carriers respectively formed by Formulation DHC2101 and Formulation DHC2501, doxorubicin and doxorubicin packaged by liposome (DO101)

| Formulation | Doxorubicin | DO101 | DHC2101 | DHC2501 |
|---|---|---|---|---|
| $IC_{50}$ (µM) | 0.1 | 1.62 | 0.17 | 0.04 |

FIG. 7 and Table 10 show that the cytotoxicity effect of hyaluronic acid derivative/doxorubicin complex nano-carriers respectively formed by Formulation DHC2101 and Formulation DHC2501 is commensurate with that of doxorubicin. According to the foregoing, the drug will still release while it is packaged, and the cytotoxicity effect of the hyaluronic acid derivative/doxorubicin complex nano-carriers respectively formed by Formulation DHC2101 and Formulation DHC2501 is significantly better than that of the control group, doxorubicin packaged by liposome (DO101).

Figure 8:
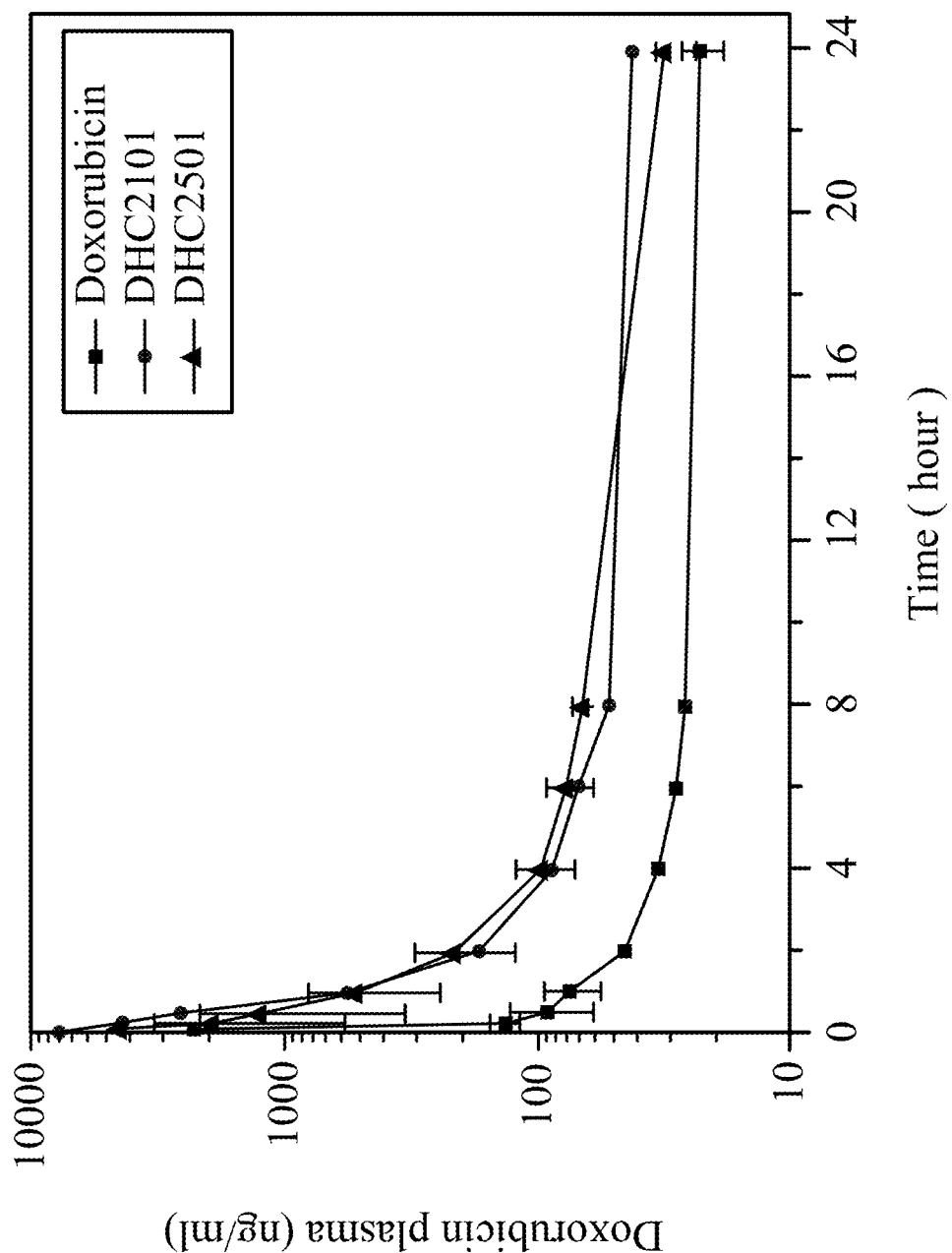
FIG. 8 shows the results of analyzing the concentration of doxorubicin in the plasma of the hyaluronic acid derivative/doxorubicin complex nano-carriers respectively formed by Formulation DHC2101 and Formulation DHC2501, and doxorubicin by LC-MS/MS according to an exemplary embodiment.

(4) Concentration Analysis of Drug Released from Hyaluronic Acid Derivative/Drug Complex Nano-Carrier in Rat Blood The rats were grouped, and 3 mg/kg the hyaluronic acid derivative/doxorubicin complex nano-carriers formed by Formulation DHC2101, the hyaluronic acid derivative/doxorubicin complex nano-carriers formed by Formulation DHC2501 and doxorubicin, were respectively administered. After that, at 5 minutes, 30 minutes, 1 hour, 2 hours, 4 hours, 8 hours and 24 hours, the blood samples were sampled from the rats, and the concentrations of doxorubicin in the plasma were analyzed by LC-MS/MS. The results are shown in FIG. 8.

The results show that, by protection of the formulation, the detention time for doxorubicin in the blood is able to be prolonged.

(5) Analysis of Inhibition of Hyaluronic Acid Derivative/Drug Complex Nano-Carrier to the Tumor in the Living Body.

U87 MG cells, human glioblastoma cell line, were implanted into the backs of nude mice. After the size of the tumor reached 100-200 mm$^3$, the mice were grouped. The mice were administered hyaluronic acid derivative/doxorubicin complex nano-carriers formed by Formulation DHC2101 (5 mg doxorubicin/kg), the hyaluronic acid derivative/doxorubicin complex nano-carriers formed by Formulation DHC2501 and doxorubicin (5 mg doxorubicin/kg) or PBS through tail vein injections twice a week, for a total of 4 doses. The size changes of the tumors were measured on a regular time schedule. The results are shown in FIG. 9

Figure 9:
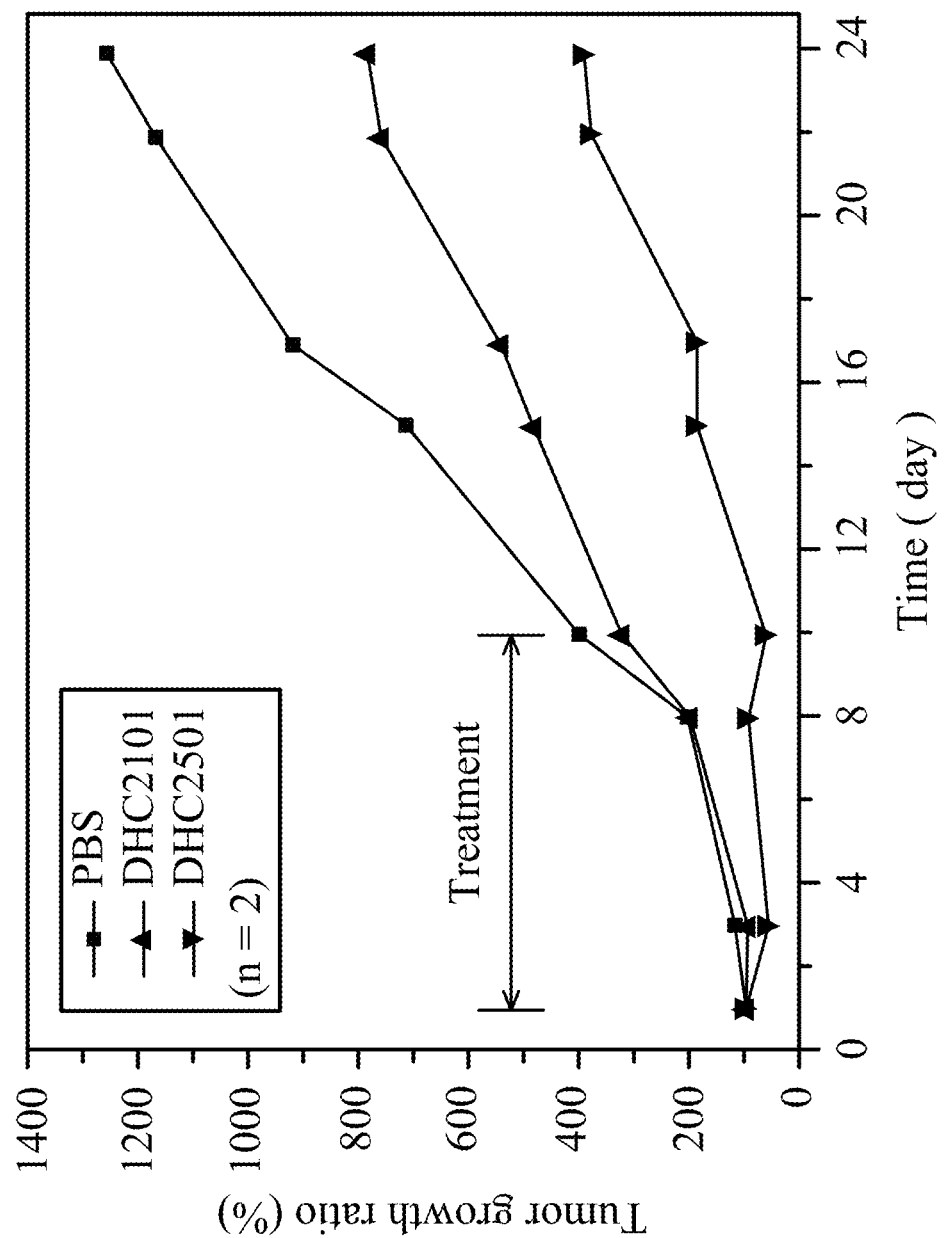
FIG. 9 shows the results of measuring tumor size of nude mice which are implanted with U87 MG cells, human glioblastoma cell line, and then treated with hyaluronic acid derivative/doxorubicin complex nano-carriers formed by Formulation DHC2101 (5 mg doxorubicin/kg), the hyaluronic acid derivative/doxorubicin complex nano-carriers formed by Formulation DHC2501 and doxorubicin (5 mg doxorubicin/kg) or PBS, respectively according to an exemplary embodiment.

According to FIG. 9, it is known that the Formulation DHC2501 has better tumor inhibiting effects.

B. Hyaluronic Acid Derivative/Dichloro(1,2-Diaminocyclohexane)Platinum (DACHPt) Complex Nano-Carrier (1) Transmission Electron Microscopy (TEM)

Figure 10:
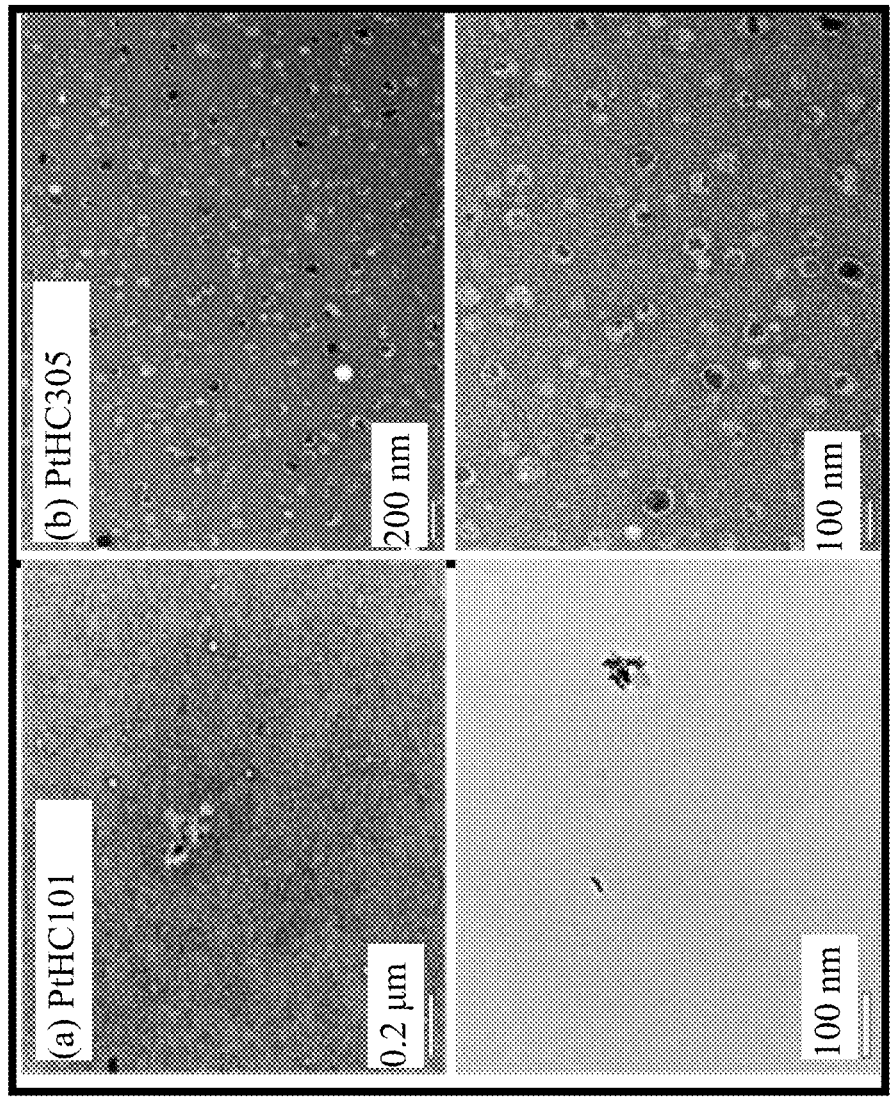
FIG. 10 shows the transmission electron microscope photographs of Hyaluronic acid/DACHPt complex nano-carrier (Formulation PtHC101) and hyaluronic acid derivative/DACHPt complex nano-carrier (Formulation PtHC305) according to an exemplary embodiment.

Hyaluronic acid/DACHPt complex nano-carrier (Formulation PtHC101) and hyaluronic acid derivative/DACHPt complex nano-carrier (Formulation PtHC305) were observed and photographed by a transmission electron microscope, and the results are shown in FIG. 10.

According to FIG. 10, it is known that the hyaluronic acid cannot package dichloro(1,2-diaminocyclohexane)platinum (DACHPt) and form a micelle. On the contrary, hyaluronic acid derivative is capable of packaging dichloro(1,2-diaminocyclohexane)platinum (DACHPt) and forming a micelle.

(2) Drug Release

Figure 11:
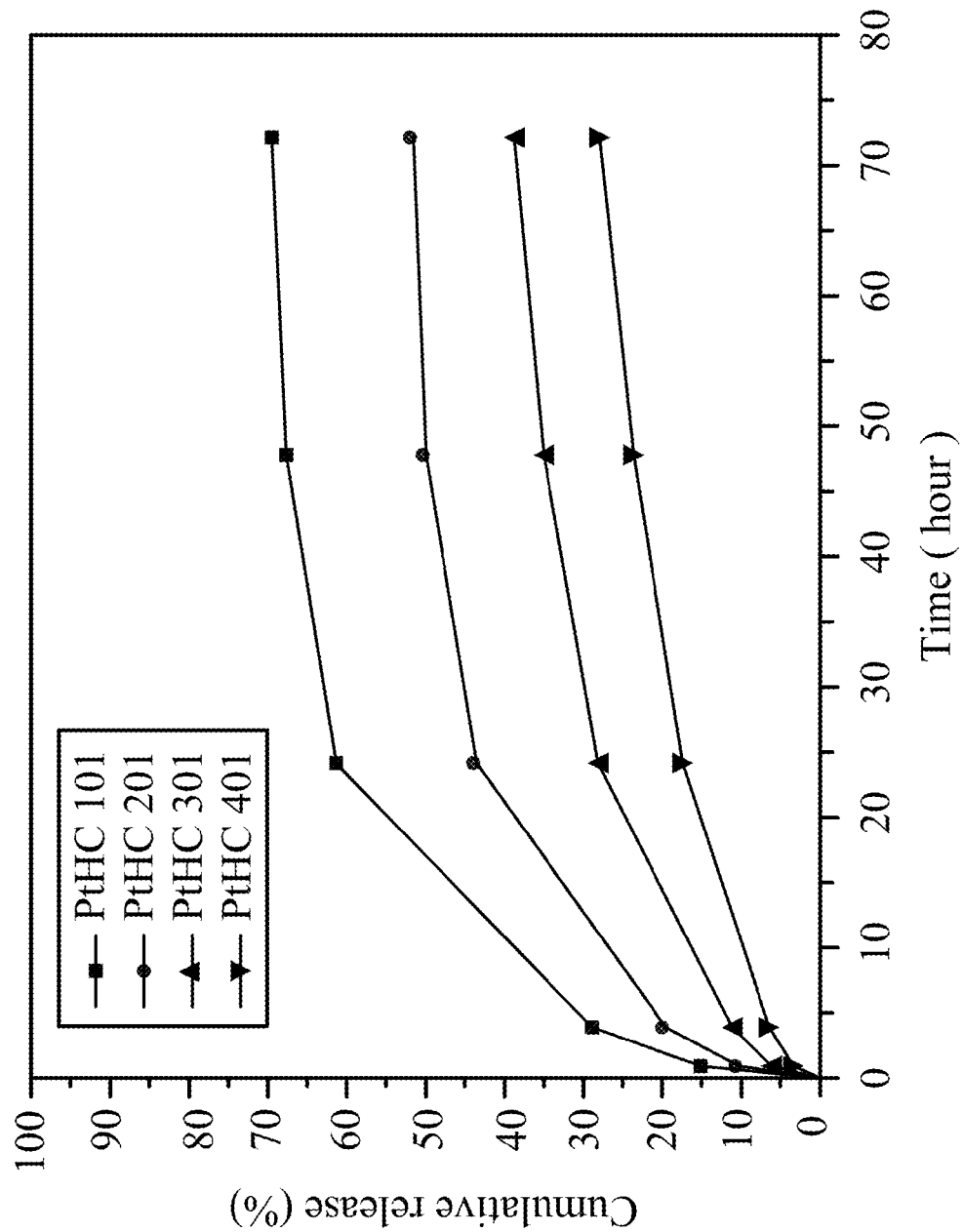
FIG. 11 shows the results of performing cumulative drug release analysis to hyaluronic acid/DACHPt complex nano-carriers formed by Formulation PtHC101 and hyaluronic acid derivative/DACHPt complex nano-carriers respectively formed by Formulations PtHC201, PtHC301 and PtHC401 at pH 7.4, respectively at pH 7.4 according to an exemplary embodiment.

Cumulative drug release analysis was performed to hyaluronic acid/DACHPt complex nano-carriers formed by Formulation PtHC101 and hyaluronic acid derivative/DACHPt complex nano-carriers respectively formed by Formulations PtHC201, PtHC301 and PtHC401 at pH 7.4 and the results are shown in FIG. 11. Detail experimental methods for the cumulative drug release analysis are described in the following.

300 μl of the formulation was placed in a dialysis bag (MWCO 3.5 kD). Next, the two opening of the dialysis bag were fixed by dialysis clamps, and the dialysis bag was placed in a bottle, and then a dialysis external solution was added in the bottle. The dialysis external solution was 15 mL of PBS with (pH 7.4). The sample bottle was placed in a thermostatic shaker incubator at 37° C. to perform drug release. The dialysis external solution was sampled 500 μl at each sampling time point. The sampled dialysis external solution was diluted 11-fold by addition of 5 mL deionized water, and then Pt concentration and quantification analysis was performed thereto by inductively coupled plasma with atomic emission spectroscopy (ICP-AES).

According to FIG. 11, it is known that the lager the amount of Boc-histidine grafted to the hyaluronic acid derivative of each formulation, the less the drug release percentage of the hyaluronic acid derivative/DACHPt complex nano-carrier is. And this shows that introduction of Boc-histidine to a material will increase the hydrophobicity of the material and influence the release ratio of the drug.

Figure 12:
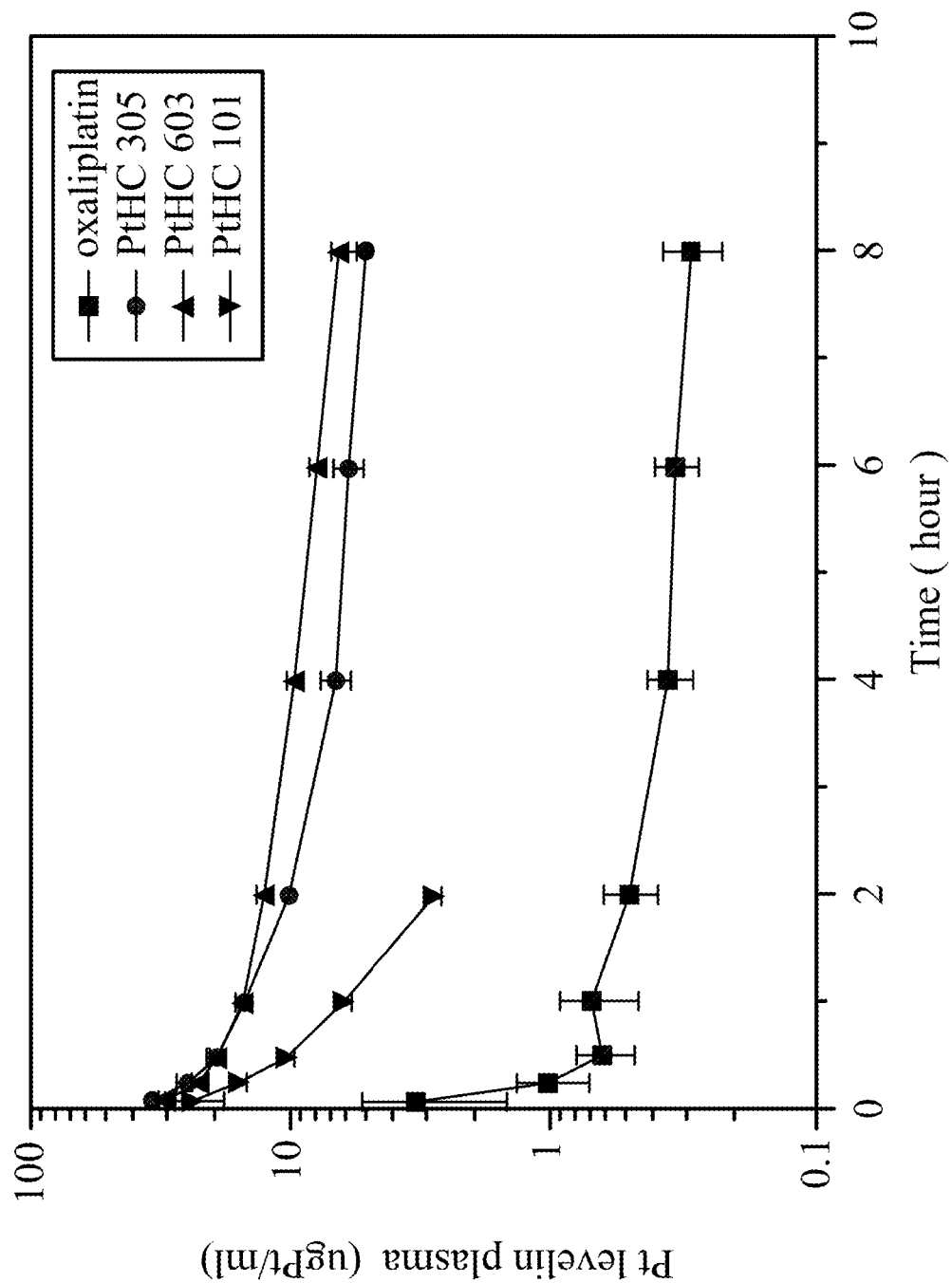
FIG. 12 shows the results of analyzing the concentration of Pt in the rat plasma of oxaliplatin, Formulations PtHC101, PtHC305 and PtHC603 by inductively coupled plasma with atomic emission spectroscopy (ICP-AES) according to an exemplary embodiment.

(3) Concentration Analysis of Drug Released from Hyaluronic Acid Derivative/Drug Complex Nano-Carrier in Rat Blood The rats were grouped, and 0.5 mg/rat oxaliplatin, Formulations PtHC101, PtHC305 and PtHC603, were respectively administered. After that, at different time points the blood samples were sampled from the rats, the concentrations of Pt in the plasma were analyzed by inductively coupled plasma with atomic emission spectroscopy (ICP-AES), and the original drug concentration in blood (CO), half-life (T ½), area under curve (AUC), volume of distribution (Vz), and clearance (Cl) of each formulation were calculated. The results are shown in FIG. 12 and Table 11.

TABLE 11

|  | Oxaliplatin | PtHC101 | PtHC305 | PtHC603 |
| --- | --- | --- | --- | --- |
| C0 (ng/ml) | 6317.9 ± 4430.9 | 30566.2 ± 12866.7 | 38419.0 ± 5899.9 | 34151.2 ± 2962.2 |
| HL_Lambda_z (hr) | 8.2 ± 1.1 | 0.8 ± 0 | 10.6 ± 1.6 | 6.3 ± 0.8 |
| Vz_pred (ml/kg) | 2620.8 ± 868.5 | 81.8 ± 4.7 | 80.6 ± 6.0 | 67.3 ± 5.3 |
| Cl_pred (ml/hr/kg) | 221.7 ± 67.6 | 69.9 ± 1.6 | 5.3 ± 0.8 | 7.4 ± 0.6 |
| AUClast (hr*ng/ml) | 4202.6 ± 1280.2 | 17774.0 ± 620.9 | 99822.2 ± 12653.9 | 90086.9 ± 3730.2 |

Compared to oxaliplatin, the hyaluronic acid derivative/DACHPt complex nano-carrier is able to decrease volume of distribution (Vz) and clearance (Cl) of Pt, and thus is able to increase area under plasma concentration-time curve of Pt (oxaliplatin v.s. PtHC101, PtHC305 and PtHC603). The results shows that by protection of the formulation, the detention time for doxorubicin in the blood is able to be prolonged, and as compared to oxaliplatin, area under plasma concentration-time curve (AUC) of the hyaluronic acid derivative/DACHPt complex nano-carrier increases about 15-20 fold.

(4) Analysis of Inhibition of Hyaluronic Acid Derivative/Drug Complex Nano-Carrier to the Tumor in the Living Body.

Figure 13:
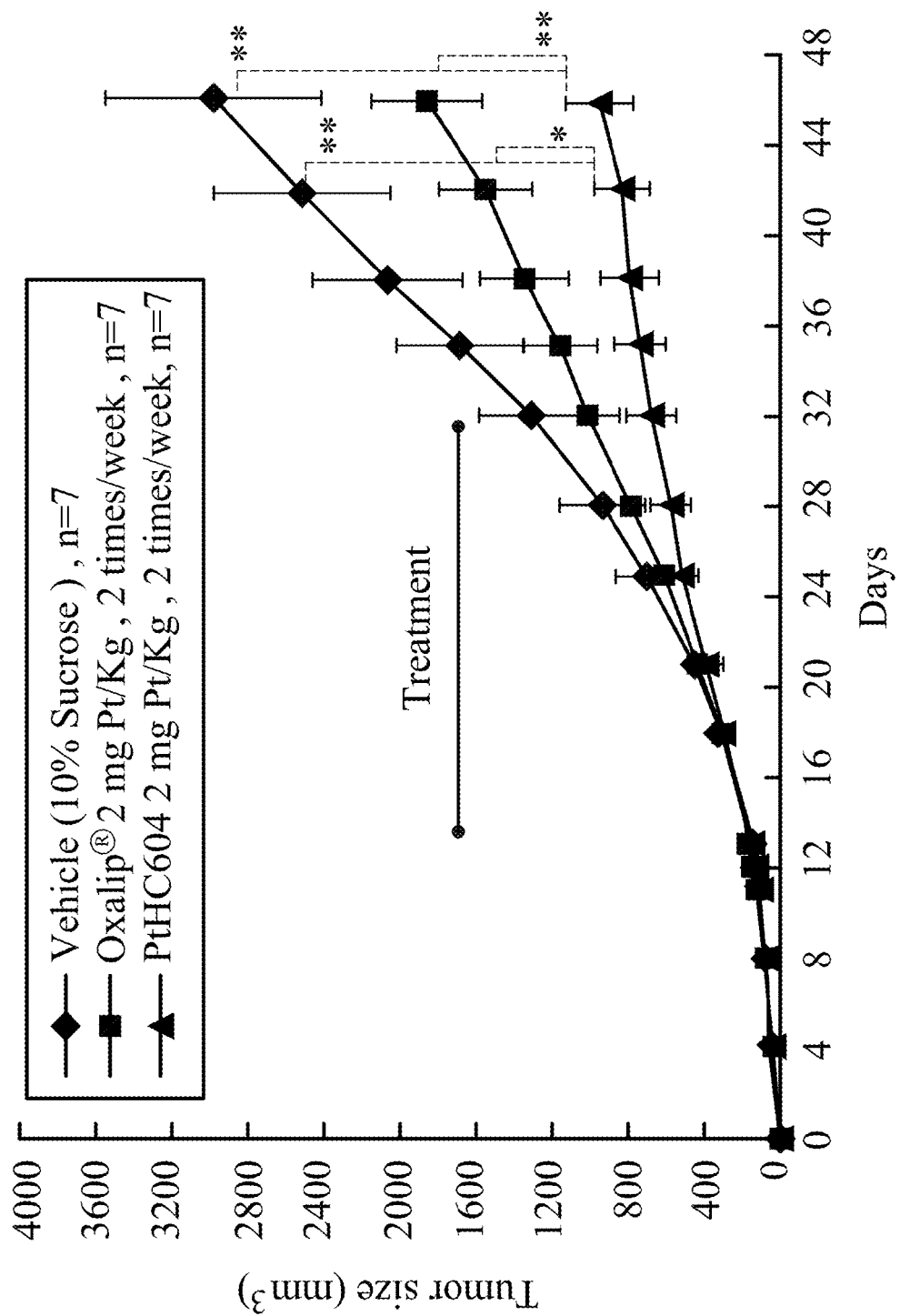
FIG. 13 shows the results of measuring tumor size of nude mice which are implanted with HT-29 cells, human colon adenocarcinoma cell line, and then treated with hyaluronic acid derivative/dichloro(1,2-diaminocyclohexane)platinum (DACHPt) complex nano-carriers formed by Formulation PtHC604 (2 mg Pt/kg), oxaliplatin (2 mg Pt/kg) and 10% sucrose, respectively according to an exemplary embodiment.

HT-29 cells, human colon adenocarcinoma cell line, were implanted into the backs of nude mice. After the size of the tumor reached 100-200 mm$^3$, the mice were administered hyaluronic acid derivative/DACHPt complex nano-carriers formed by Formulation PtHC604 (2 mg Pt/kg), oxaliplatin (2 mg Pt/kg) or 10% sucrose through tail vein injections twice a week, for a total of 6 doses. The size changes of the tumors were measured, regularly, and tumor growth inhibition (TGI) rate was calculated. The results are shown in FIG. 13. Calculation formula is as follows:

Tumor growth inhibition (TGI) (%)=[1−(Δ Tumor volume for drug treatment group/Δ Tumor volume for vehicle treatment group)]×100

According to FIG. 13, it is known that the hyaluronic acid derivative/DACHPt complex nano-carriers formed by Formulation PtHC604 have a better inhibiting effect to tumor growth. From day 14 to day 42, tumor growth inhibition (TGI) rate for mice administered with the hyaluronic acid derivative/DACHPt complex nano-carriers formed by Formulation PtHC604 is 72±4%; conversely, tumor growth inhibition (TGI) rate for mice administered with the oxaliplatin is only 42±8%. There is a statistical difference between the two groups. (p<0.05). The results mentioned above once again demonstrate that nano-carriers prepared by the disclosure have a better tumor inhibiting effect.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A biomedical composition, comprising:
   a hyaluronic acid;
   a modified histidine, wherein the modified histidine is Boc-histidine, Cbz-histidine, Fmoc-histidine or Ac-histidine; and
   a polymer or $C_4$-$C_{20}$ alkane,
   wherein the modified histidine and the polymer or $C_4$-$C_{20}$ alkane are grafted to at least one primary hydroxyl group of the hyaluronic acid to allow the hyaluronic acid to form a hyaluronic acid derivative, and
   wherein a graft ratio of the modified histidine is about 1-100%, and a graft ratio of the polymer or $C_4$-$C_{20}$ alkane is about 0-40%.

2. The biomedical composition as claimed in claim 1, wherein a molecular weight of the hyaluronic acid is about 7,000-1,500,000.

3. The biomedical composition as claimed in claim 1, wherein a graft ratio of the modified histidine is about 1-100%, and a graft ratio of the polymer or $C_4$-$C_{20}$ alkane is 0.

4. The biomedical composition as claimed in claim 1, wherein the modified histidine is Boc-histidine, and a graft ratio of the Boc-histidine is about 1-100%, and a graft ratio of the polymer or $C_4$-$C_{20}$ alkane is 0.

5. The biomedical composition as claimed in claim 1, wherein the polymer is polyethylene glycol (PEG), polycaprolactone (PCL), poly lactic acid (PLA), polyglycolic acid (PGA), poly(lactic-co-glycolic acid)(PLGA) or polyvinylpyrrolidone (PVP).

6. The biomedical composition as claimed in claim 1, wherein the polymer is polyethylene glycol (PEG), and a graft ratio of the polyethylene glycol (PEG) is about 1-40%.

7. The biomedical composition as claimed in claim 6, wherein the modified histidine is Boc-histidine, and
   wherein a graft ratio of the Boc-histidine is about 1-80%, and a graft ratio of the polyethylene glycol (PEG) is about 1-30%.

8. The biomedical composition as claimed in claim 1, wherein the $C_4$-$C_{20}$ alkane is $C_5H_{11}$, $C_7H_{15}$, $C_9H_{19}$ or $C_{11}H_{23}$.

9. The biomedical composition as claimed in claim 1, wherein the $C_4$-$C_{20}$ alkane is $C_{11}H_{23}$, and a graft ratio of the $C_{11}H_{23}$ is about 1-40%.

10. The biomedical composition as claimed in claim 9, wherein the modified histidine is Boc-histidine, and a graft ratio of the Boc-histidine is about 1-80%, and a graft ratio of the $C_{11}H_{23}$ is about 1-30%.

11. The biomedical composition as claimed in claim 1, further comprising an active ingredient with a positive charge in water.

12. The biomedical composition as claimed in claim 11, wherein a weight ratio of the hyaluronic acid derivative to the active ingredient with a positive charge in water is about 1.25:1-50:1.

13. The biomedical composition as claimed in claim 11, wherein the active ingredient with a positive charge in water is doxorubicin, irinotecan, gentamicin or a platinum compound.

14. The biomedical composition as claimed in claim 13, wherein the platinum compound is dichloro(1,2-diaminocyclohexane)platinum (DACHPt), cisplatin or oxaliplatin.

15. The biomedical composition as claimed in claim 11, wherein the modified histidine is Boc-histidine, a graft ratio of the polymer or $C_4$-$C_{20}$ alkane is 0,and the active ingredient with a positive charge in water is doxorubicin, irinotecan, gentamicin or dichloro(1,2-diaminocyclohexane)platinum (DACHPt).

16. The biomedical composition as claimed in claim 15, wherein a graft ratio of the Boc-histidine is about 1-80%, and a weight ratio of the hyaluronic acid derivative to the active ingredient with a positive charge in water is about 1.25:1-25:1.

17. The biomedical composition as claimed in claim 11, wherein the modified histidine is Boc-histidine, the polymer is polyethylene glycol (PEG), and the active ingredient with a positive charge in water is doxorubicin, irinotecan, gentamicin or dichloro(1,2-diaminocyclohexane)platinum (DACHPt).

18. The biomedical composition as claimed in claim 17, wherein a graft ratio of the Boc-histidine is about 1-80%, a graft ratio of the polyethylene glycol (PEG) is about 1-30%, and a weight ratio of the hyaluronic acid derivative to the active ingredient with a positive charge in water is about 3:1-50:1.

19. The biomedical composition as claimed in claim 11, wherein the modified histidine is Boc-histidine, the $C_4$-$C_{20}$ alkane is $C_{11}H_{23}$, and the active ingredient with a positive charge in water is doxorubicin, irinotecan, gentamicin or dichloro(1,2-diaminocyclohexane)platinum (DACHPt).

20. The biomedical composition as claimed in claim 19, wherein a graft ratio of the Boc-histidine is about 1-80%, a graft ratio of the $C_{11}H_{23}$ is about 1-30%, and a weight ratio of the hyaluronic acid derivative to the active ingredient with a positive charge in water is about 2.5:1-4:1.

* * * * *